US006657027B2

(12) United States Patent
Ostoja-Starzewski et al.

(10) Patent No.: US 6,657,027 B2
(45) Date of Patent: Dec. 2, 2003

(54) CATALYSTS WITH A DONOR-ACCEPTOR INTERACTION

(75) Inventors: Karl-Heinz Aleksander Ostoja-Starzewski, Bad Vilbel (DE); Bruce S. Xin, Yokohama (JP)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/100,338

(22) Filed: Mar. 18, 2002

(65) Prior Publication Data

US 2003/0036474 A1 Feb. 20, 2003

(30) Foreign Application Priority Data

Mar. 23, 2001 (DE) .......................... 101 14 345

(51) Int. Cl.$^7$ ............................ C08F 4/64; B01J 31/00; C07F 17/00
(52) U.S. Cl. ............................ 526/161; 556/7; 556/13; 556/27; 556/52; 556/53; 502/103; 502/152; 502/155; 526/133; 526/134; 526/351; 526/943
(58) Field of Search ............................ 556/7, 13, 27, 556/52, 53; 502/103, 152, 155; 526/133, 134, 161, 351, 943

(56) References Cited

U.S. PATENT DOCUMENTS

| 5,807,936 | A | 9/1998 | Fritze et al. ............... 526/126 |
|---|---|---|---|
| 5,854,166 | A | 12/1998 | Marks et al. ............... 502/153 |
| 5,962,718 | A | 10/1999 | Reetz et al. ............... 556/51 |
| 6,130,302 | A | 10/2000 | Marks et al. ............... 526/127 |
| 6,232,413 | B1 * | 5/2001 | Starzewski et al. |
| 6,353,064 | B1 | 3/2002 | Ostoja-Starzewski ....... 526/160 |
| 6,423,659 | B1 * | 7/2002 | Starzewski et al. |
| 6,433,112 | B1 * | 8/2002 | Ostoja-Starzewski et al. |

FOREIGN PATENT DOCUMENTS

| EP | 0 704 461 | 3/2001 |
|---|---|---|
| EP | 0 129 368 | 4/2002 |
| GB | 2 303 367 | 2/1997 |
| WO | 94/20506 | 9/1994 |
| WO | 98/01455 | 1/1998 |
| WO | 98/01456 | 1/1998 |
| WO | 98/01483 | 1/1998 |
| WO | 98/01484 | 1/1998 |
| WO | 98/01487 | 1/1998 |
| WO | 98/06759 | 2/1998 |
| WO | 98/45339 | 10/1998 |
| WO | 99/14222 | 3/1999 |
| WO | 99/64476 | 12/1999 |
| WO | 99/009514 | 2/2000 |
| WO | 00/35973 | 6/2000 |
| WO | 00/37513 | 6/2000 |

OTHER PUBLICATIONS

Bochmann, Manfred et al: "Anionic and Zwitterionic metallocene complexes derived from novel boratocyclopentadienyl ligands" J. Chem. Soc., Chem. Commun. (1995), (20), 2081–2 XP001074054 Schema 1; Verbindungen 3a–c, 4a–c, 6 Schema 2; Edukt und Prodkt Seite 2081.

Reetz, Manfred T. et al: "Preparation and catalytic activity of boron–substituted zirconocenes" Chimia (1995), 49 (12), 501–3 XP008005572 Schema 2, Verbindungen 4c und 5c Seite 501.

Duchateau, Robbert et al; "Synthesis of Cyclopentadienyl–, Indenyl–, and Fluorenylbis(pentaflurophenyl) Boranes as Ligands in Titanium and Zirconium Half–Sandwich Complexes. The Crystal Structures of C13H9B(C6F5)2.cntdot.t–BuNH2!, C13H8SiMe3B(C6F5)2!, and {.eta.5–C4H4B(C5F5)2}TiC13" Organomettallics, Bd. 16, Nr. 23, 1997, Seiten 4995–5005, XP001089836 Seite 4999; Tabelle 1 Seite 5003; Abbildung 3.

Lancaster, Simon J. et al: "Borato–Cyclopentadienyl Half–Sandwich Complexes. Crystal Structures of 'Net4!'C5H5B(C6F5)3·.cntdot.CH2C12 and 'Net4!2' {C5H4B(C6F5)3}Zr(.mu.–C1)C12!2" Organometallics, Bd. 17, Nr. 18, 1998, Seiten 3829–3831, XP001089833 Seite 3830 –Seite 3831.

Harlan, C. Jeff et al: "The One–Electron Oxidation of an Azazirconacyclobutene in the Presence of B(C6F5)3" Journal of the American Chemical Society (1999), 121(31), 7274–7275, XP001089842 Verbindung 4 Seite 7275.

Braunschweig, Holger et al: "Reactions of (.eta.5–C5R5) 2WH2! with boranes" Zeitschrift Fuer Naturforschung, B: Chemical Sciences (1999), 54(7), 839–842, XP001074055 Seite 839.

Doerrer, Linda H. Et Al: "Electrophilic addition reactions of the Lewis acids B(C6F5)2R R =C6F5, Ph, H or Cl! with the metallocene hydrides M(.eta. –C5H5(2H2! (M = Mo or W), Re(.eta. –C5H5)2H! and Ta (.eta. –C5H5)2H3!" Dalton (2000), (5), 813–820, XP001009404 Seite 815; Abbildung 1.

Lancaster, Simon J. Et Al: "Synthetic, Reactivity, and Structural Studies on Borylcyclonpentadienyl Complexes of Titanium: New CpB Titanocene Complexes with C–B–Cl, C–B–O, and C–B–N Bridges (CpB =.eta.5–C5H4B(C6F5)2)" Organomettallics (2000), 19(8), 1599–1608, XP001089861 Seite 1601 –Seite 1602; Tabelle 1.

(List continued on next page.)

Primary Examiner—Caixia Lu
(74) Attorney, Agent, or Firm—Joseph C. Gil; Noland J. Cheung; Jennifer R. Seng

(57) ABSTRACT

The present invention relates to compounds in which a transition metal is complexed with two ligand systems and the two systems are reversibly bonded together by at least one bridge consisting of a donor and an acceptor, at least one substituent on the acceptor group being a fluorinated aryl radical, to the use of these compounds as catalysts and to a process for the polymerization of olefins.

21 Claims, No Drawings

OTHER PUBLICATIONS

Carpenter, Bryon E. Et Al: "Synthesis of the diborylated ferrocene 1,1'–bis bis(pentafluorophenyl) bor 1!ferrocence and the x–ray structure of its trimethylphosphine adduct" Canadian Journal of Chemistry (2001), 79(3), 291–295, Marz 2001 (Mar. 2001), XP001074056 Seite 292.

Carpenter, Bryon E. Et Al: "Synthesis, characterization and chemistry of bis–(pentafluorophenyl)boryl ferrocene" Canadian Journal Of Chemistry (2001), 79(5/6), 857–867, Jul. 5, 2001, XP001074058 Seite 861.

Liu, Shengming Et. Al: "Formation of Triniobocene Cationic and Neutral Mononiobocene Species as a Function of Solvent in the Reaction of Cp2Nb {.mu. –H)2BR2} (R2 = C4H8, C5H10, C8H14) with B(C6F5)3" Organometallics, Bd. 20, Nr. 26, Nov. 21, 2001, Seiten 5717–5723, XP001089860 Reaktion (2), Verbindung 2 Seite 5719.

* cited by examiner

CATALYSTS WITH A DONOR-ACCEPTOR INTERACTION

FIELD OF THE INVENTION

The present invention relates to compounds in which a transition metal is complexed with two ligand systems and the two systems are reversibly bonded together by at least one bridge containing a donor and an acceptor, at least one substituent on the acceptor group being a fluorinated aryl radical, to the use of these compounds as catalysts and to a process for the polymerization of olefins.

BACKGROUND OF THE INVENTION

The coordinate bond existing between the donor atom and the acceptor atom produces a (partial) positive charge in the donor group and a (partial) negative charge in the acceptor group:

[donor group ⟶ acceptor group]

The invention further relates to the use of these catalysts with a donor-acceptor interaction as polymerization catalysts.

Metallocenes as π complex compounds and their use as catalysts in the polymerization of olefins have been known for a long time (EP-A-129 368 and the literature cited therein). It is also known from EP-A-129 368 that metallocenes, in combination with alkylaluminum/water as co-catalysts, are effective systems for the polymerization of ethylene, (thus, for example, methylaluminoxane=MAO is formed from approx. 1 mol of trimethylaluminum and 1 mol of water). Other stoichiometric proportions have also already been used successfully (WO 94/20506)). Metallocenes whose cyclopentadienyl skeletons are covalently linked together by a bridge are also already known. EP-A-704 461 may be cited as an example of the numerous patents and patent applications in this field, the linking group mentioned in said patent being a (substituted) methylene group or ethylene group, a silylene group, a substituted silylene group, a substituted germylene group or a substituted phosphine group. EP-A-704 461 also provides the bridged metallocenes as polymerization catalysts for olefins.

Catalysts with a donor-acceptor interaction and their use as polymerization catalysts are known in principle.

Thus, WO-A-98/01455 describes compounds in which a transition metal is complexed with two π systems, especially with aromatic π systems (metallocenes), and the two systems are reversibly bonded together by at least one bridge containing a donor and an acceptor, the donor or acceptor atoms being bonded as substituents on the π systems; it also describes their use as polymerization catalysts.

WO-A-98/45339 describes compounds in which a transition metal is complexed with two π systems, especially with aromatic π systems (metallocenes), and the two systems are reversibly bonded together by at least one bridge containing a donor and an acceptor, at least one of the donor or acceptor atoms being part of the respective π system; it also describes their use as polymerization catalysts.

Patent applications WO-A-98/01483 to WO-A-98/01487 describe industrial polymerization processes which use the described catalysts with a donor-acceptor interaction.

It is known from said documents that the catalysts with a donor-acceptor interaction can advantageously be used as catalysts for the polymerization of olefins.

However, it was a surprise to those skilled in the art that particularly advantageous catalysts with a donor-acceptor interaction could be prepared by selecting special substitution patterns on the acceptor group.

SUMMARY OF THE INVENTION

Therefore, the present invention provides transition metal compounds with two π systems and at least one donor-acceptor interaction between these π systems, characterized in that these transition metal compounds have at least one fluorine-substituted aryl group on at least one acceptor atom.

DETAILED DESCRIPTION OF THE INVENTION

π systems according to the present invention are substituted and unsubstituted ethylene, allyl, pentadienyl, benzyl, butadiene, benzene, the cyclopentadienyl anion and species produced by replacing at least one C atom with a heteroatom, said species preferably being cyclic. The coordination of such ligands (π systems) to the metal can be of the σ type or of the π type.

Suitable transition metal compounds with at least one donor-acceptor interaction are the transition metal compounds with a donor-acceptor interaction described in patent applications WO-A-98/01455, WO-A-98/45339 and WO-A-98/01483 to WO-A-98/01487, characterized in that these transition metal compounds have fluorine-substituted aryl groups on the acceptor group.

Particularly suitable compounds are the metallocenes of the formula

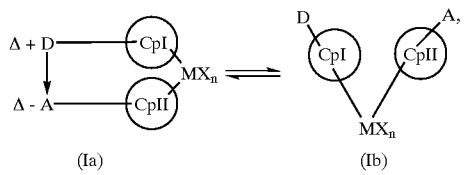

(Ia)       (Ib)

in which

CpI and CpII are two identical or different carbanions with a cyclopentadienyl-containing structure, in which one to all of the H atoms can be substituted by identical or different radicals from the group comprising linear or branched $C_1$–$C_{20}$-alkyl which can be monosubstituted to fully substituted by halogen, monosubstituted to trisubstituted by phenyl and monosubstituted to trisubstituted by vinyl, $C_6$–$C_{12}$-aryl, halogenoaryl having 6 to 12 C atoms, and organometallic substituents such as silyl, trimethylsilyl and ferrocenyl, and can be monosubstituted or disubstituted by D and A, D is a donor atom which can additionally carry substituents and which, in its respective bonding state, has at least one free electron pair, A is an acceptor atom which carries at least one fluorine-substituted aryl group, but preferably exclusively fluorine-substituted aryl groups, as substituents and which, in its respective bonding state, has an electron pair deficiency, D and A being linked by a reversible coordinate bond in such a way that the donor group assumes a (partial) positive charge and the acceptor group a (partial) negative charge, M is a metal of groups III–VII of the periodic table of the elements as defined by IUPAC (1985), including the lanthanides and actinides, X is one anion equivalent and n is the number zero, one, two, three or four, depending on the charge of M.

The first and second carbanions CpI and CpII with a cyclopentadienyl skeleton can be identical or different. The cyclopentadienyl skeleton can for example be one of the group of cyclopentadiene, substituted cyclopentadiene, indene, substituted indene, fluorene and substituted fluorene, wherein fluorene and substituted fluorene are preferred. There may be 1 to 4 substituents per cyclopentadiene ring or fused benzene ring. These substituents can be $C_1$–$C_{20}$-alkyl such as methyl, ethyl, propyl, isopropyl, butyl or isobutyl, hexyl, octyl, decyl, dodecyl, hexadecyl, octadecyl or eicosyl, $C_1$–$C_{20}$-alkoxy such as methoxy, ethoxy, propoxy, isopropoxy, butoxy or isobutoxy, hexyloxy, octyloxy, decyloxy, dodecyloxy, hexadecyloxy, octadecyloxy or eicosyloxy, halogens such as fluorine, chlorine or bromine, $C_6$–$C_{12}$-aryl such as phenyl, $C_1$–$C_4$-alkylphenyl such as tolyl, ethylphenyl, (i-)propylphenyl, (i-/tert-)butylphenyl or xylyl, halogenophenyl such as fluoro-, chloro- or bromophenyl, difluorophenyl, trifluorophenyl, tetrafluorophenyl, pentafluorophenyl, pentachlorophenyl, naphthyl or biphenylyl, triorganylsilyl such as trimethylsilyl (TMS), ferrocenyl, and D or A, as defined above. Fused aromatic rings can also be partially or completely hydrogenated, leaving only the double bond to which both the fused ring and the cyclopentadiene ring contribute. Furthermore, benzene rings, as in indene or fluorene, can carry one or two additional fused benzene rings. Also, the cyclopentadiene or cyclopentadienyl ring and a fused benzene ring can together carry an additional fused benzene ring. In the form of their anions, such cyclopentadiene skeletons are excellent ligands for transition metals, each cyclopentadienyl carbanion of said optionally substituted form compensating one positive charge of the central metal in the complex.

Specific examples of such carbanions are cyclopentadienyl, methylcyclopentadienyl, 1,2-dimethylcyclopentadienyl, 1,3-dimethylcyclopentadienyl, indenyl, phenylindenyl, 1,2-diethylcyclopentadienyl, tetramethylcyclopentadienyl, ethylcyclopentadienyl, n-butylcyclopentadienyl, n-octylcyclopentadienyl, β-phenylpropylcyclopentadienyl, tetrahydroindenyl, propylcyclopentadienyl, t-butylcyclopentadienyl, benzylcyclopentadienyl, diphenylmethylcyclopentadienyl, trimethylgermylcyclopentadienyl, trimethylstannylcyclopentadienyl, trifluoromethylcyclopentadienyl, trimethylsilylcyclopentadienyl, pentamethylcyclopentadienyl, fluorenyl, tetrahydro- or octahydrofluorenyl, fluorenyls and indenyls benzo-fused on the six-membered ring, N,N-dimethylaminocyclopentadienyl, dimethylphosphinocyclopentadienyl, methoxycyclopentadienyl, dimethylboranylcyclopentadienyl and (N,N-dimethylamino-methyl)cyclopentadienyl.

The subscript n assumes a value of zero, one, two, three or four, preferably zero, one or two, depending on the charge of M. Depending inter alia on which of the subgroups they belong to, the above-mentioned metals of groups III–VII can have valencies/charges of two to six, preferably two to four, two of which are compensated in each case by the carbanions of the metallocene compound. Accordingly, in the case of $La^{3+}$, $Zr^{4+}$ and $Sm^{2+}$, the subscript n assumes a value of one, two and zero, respectively.

Reference is made to WO-A-98/45339 for the preparation of the compounds (I).

Other particularly suitable compounds are the metallocenes of formula (II):

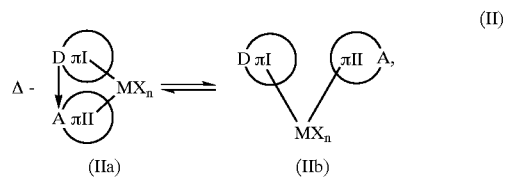

(II)

in which

πI and πII are mutually different, charged or electrically neutral π systems which can be fused with one or two unsaturated or saturated five-membered or six-membered rings, D is a donor atom which is a substituent of πI or part of the π system of πI and which, in its respective bonding state, has at least one free electron pair, A is an acceptor atom which is a substituent of πII or part of the π system of πII and which, in its respective bonding state, has an electron pair deficiency, D and A being linked by a reversible coordinate bond in such a way that the donor group assumes a (partial) positive charge and the acceptor group a (partial) negative charge, and at least one of D and A being part of the respective π system, it being possible for D in turn to carry substituents, and A carrying at least one fluorine-substituted aryl group, but preferably exclusively fluorine-substituted aryl groups, as substituents, it being possible for each π system or each fused ring system to contain one or more D or A, or D and A, and it being possible, in πI and πII in the non-fused or fused form, for one to all of the H atoms of the π system independently of one another to be substituted by identical or different radicals from the group comprising linear or branched $C_1$–$C_{20}$-alkyl which can be monosubstituted to fully substituted by halogen, monosubstituted to trisubstituted by phenyl and monosubstituted to trisubstituted by vinyl, $C_6$–$C_{12}$-aryl and halogenoaryl having 6 to 12 C atoms, and to be monosubstituted or disubstituted by D and A, so that the reversible D→A coordinate bond is formed between D and A where (i) both D and A are parts of the respective π system or fused ring system, or (ii) D or A is part of the π system or fused ring system and the other one is a substituent of the non-fused π system or fused ring system, or (iii) both D and A are such substituents, whereby, in the case of (iii), at least one additional D or A, or both, is (are) part of the π system or fused ring system, M is a metal of groups III–VII of the periodic table of the elements as defined by IUPAC (1985), including the lanthanides and actinides, X is one anion equivalent and n is the number zero, one, two, three or four, depending on the charges of M and those of πI and πII.

π systems according to the present invention are substituted and unsubstituted ethylene, allyl, pentadienyl, benzyl, butadiene, benzene, the cyclopentadienyl anion and species produced by replacing at least one C atom with a heteroatom, said species preferably being cyclic. The coordination of such ligands (π systems) to the metal can be of the σ type or of the π type.

More preferred sandwich structures are those in which both the π systems are selected from cyclopentadienyl (cp), indenyl (ind) and fluorenyl (flu), especially:

cp-cp cp-ind cp-flu ind-ind
ind-flu
flu-flu

The subscript n assumes a value of zero, one, two, three or four, preferably zero, one or two, depending on the charge of M. Depending inter alia on which of the subgroups they belong to, the above-mentioned subgroup metals can have valencies/charges of two to six, preferably two to four, two of which are compensated in each case by the carbanions of the metallocene compound. Accordingly, in the case of $La^{3+}$, $Zr^{4+}$ and $Sm^{2+}$, the subscript n assumes a value of one, two and zero, respectively.

In the formation of the metallocene structure of formula (I) or (II) above, one positive charge of the transition metal M is compensated by one cyclopentadienyl-containing carbanion. Positive charges still remaining on the central atom M are neutralized by other, usually monovalent anions X, it also being possible for two identical or different such anions to be linked together (dianions $\frown_{x\;x}$) examples being singly or doubly negatively charged radicals from identical or different, linear or branched, saturated or unsaturated hydrocarbons, amines, phosphines, thioalcohols, alcohols or phenols. Singly charged anions, such as $CR_3^-$, $NR_2^-$, $PR_2^-$, $OR^-$, $SR^-$ etc., can be bonded together by saturated or unsaturated hydrocarbon or silane bridges to form dianions, it being possible for the number of bridging atoms to be 0, 1, 2, 3, 4, 5 or 6, preferably 0 to 4 and more preferably 1 or 2. Apart from H atoms, the bridging atoms can carry further hydrocarbon substituents R. Examples of bridges between the singly charged anions are —$CH_2$—, —$CH_2$—$CH_2$—, —$(CH_2)_3$—, —$CH=CH$—, —$(CH=CH)_2$—, —$CH=CH$—$CH_2$—, —$CH_2$—$CH=CH$—$CH_2$—, —$Si(CH_3)_2$— and —$C(CH_3)_2$—. Examples of X are hydride, chloride, methyl, ethyl, phenyl, fluoride, bromide, iodide, the n-propyl radical, the i-propyl radical, the n-butyl radical, the amyl radical, the i-amyl radical, the hexyl radical, the i-butyl radical, the heptyl radical, the octyl radical, the nonyl radical, the decyl radical, the cetyl radical, methoxy, ethoxy, propoxy, butoxy, phenoxy, dimethylamino, diethylamino, methylethylamino, di-t-butylamino, diphenylamino, diphenylphosphino, dicyclohexylphosphino, dimethylphosphino, methylidene, ethylidene, propylidene and the ethylene glycol dianion. Examples of dianions are 1,4-diphenyl-1,3-butadienediyl, 3-methyl-1,3-pentadienediyl, 1,4-dibenzyl-1,3-butadienediyl, 2,4-hexadienediyl, 1,3-pentadienediyl, 1,4-ditolyl-1,3-butadienediyl, 1,4-bis(trimethylsilyl)-1,3-butadienediyl and 1,3-butadienediyl. 1,4-Diphenyl-1,3-butadienediyl, 1,3-pentadienediyl, 1,4-dibenzyl-1,3-butadienediyl, 2,4-hexadienediyl, 3-methyl-1,3-pentadienediyl, 1,4-ditolyl-1,3-butadienediyl and 1,4-bis(trimethylsilyl)-1,3-butadienediyl are particularly preferred. Other examples of dianions are those with heteroatoms, for instance of the structure

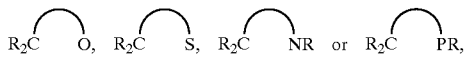

the bridge being defined as indicated. Other particularly preferred anions for charge compensation are weakly coordinating or non-coordinating anions of the above-mentioned type or singly negatively charged anions of the CpI, CpII, πI or πII type with the possible substitutions already described, which can but do not have to carry additional D or A substituents.

The compounds of general formula (II) can be prepared as described in WO-A-98/45339.

As well as the obligatory first donor-acceptor bond between D and A in formulae (I) and (II), other donor-acceptor bonds can be formed if additional D and/or A are present as substituents of the respective cyclopentadiene systems. All the donor-acceptor bonds are characterized by their reversibility illustrated above. In the case where there are several D or A, these can occupy different positions among those mentioned. Accordingly, the present invention encompasses not only the bridged molecular states but also the non-bridged states. The number of D groups can be identical to or different from the number of A groups. Preferably, the ligands, especially CpI and CpII, are linked together by only one donor-acceptor bridge.

In addition to the D/A bridges according to the present invention, covalent bridges can also be present in formulae (I) and (II). In this case, the D/A bridges strengthen the stereorigidity and thermal stability of the catalyst. By changing between closed and open D/A bonds, it is possible to obtain block polymers of higher and lower stereoregularity. Such blocks can have different chemical compositions in copolymers.

Possible donor groups in formulae (I) and (II) are particularly those in which the donor atom D is an element of group XV, XVI or XVII of the periodic table of the elements and has at least one free electron pair, and in which the donor atom is in a bonding state with substituents in the case of elements of group XV and can be in such a state in the case of elements of group XVI; donor atoms of group XVII do not carry substituents. This is illustrated below using phosphorus, P, oxygen, O, and chlorine, Cl, as examples of donor atoms, where "Subst." represents said substituents, "-Cp" represents the bond to the cyclopentadienyl-containing carbanion, a line with an arrowhead denotes a coordinate bond as in formula (I) or (II) and other lines denote available electron pairs:

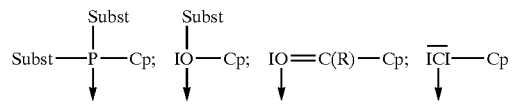

Possible acceptor groups in formulae (I) and (II) are especially those in which the acceptor atom A is an element of group XIII of the periodic table of the elements (as defined by IUPAC, 1985), such as boron, aluminum, gallium, indium and thallium, is in a bonding state with substituents and has an electron deficiency.

D and A are linked by a coordinate bond (also known as a dative bond), D assuming a (partial) positive charge and A a (partial) negative charge.

Accordingly, a distinction is drawn between the donor atom D and the donor group and between the acceptor atom A and the acceptor group. The coordinate bond D→A is formed between the donor atom D and the acceptor atom A. The donor group denotes the unit made up of the donor atom D, any substituents present and the available electron pairs; correspondingly, the acceptor group denotes the unit made up of the acceptor atom A, the substituents and the available electron deficiency.

Donor groups are groups in which the free electron pair is located on N, P, As, Sb, Bi, O, S, Se, Te, F, Cl, Br or I, preference being given to N, P, O and S. Examples of donor groups which may be mentioned are $(CH_3)_2N$—, $(C_2H_5)_2N$—, $(C_3H_7)_2N$—, $(C_4H_9)_2N$—, $(C_6H_5)_2N$—, $(CH_3)_2P$—, $(CH_2H_5)_2P$—, $(C_3H_7)_2P$—, $(i-C_3H_7)_2P$—, $(C_4H_9)_2P$—, $(t-C_4H_9)_2P$—, $(cyclohexyl)_2P$—, $(C_6H_5)_2P$—, $(CH_3)(C_6H_5)P$—, $(CH_3O)_2P$—, $(C_2H_5O)_2P$—, $(C_6H_5O)_2P$—, ($CH_3$–$C_6H_4O$)$_2$P—, (($CH_3$)$_2$N)$_2$P—, methyl-containing phosphino groups, $CH_3O$—, $CH_3S$—, $C_6H_5S$—, —C($C_6H_5$)=O, —C($CH_3$)=O, —OSi($CH_3$)$_3$ and —OSi($CH_3$)$_2$-t-butyl, N and P each carrying one free electron pair and O and S each carrying two free electron pairs, and the double-bonded oxygen in the last two examples being bonded via a spacer group, as well as systems like the pyrrolidone ring, the ring members other than N also acting as spacers. Acceptor groups are groups in which an electron pair deficiency is present on B, Al, Ga, In or Tl, preferably B, Al or Ga; examples which may be mentioned are ($C_6F_5$)$_2$B—, ($C_6F_5$)(alkyl)B—, ($C_6F_5$)HB—, ($C_6F_5$)($C_6H_5$)B—, ($CH_3$)($C_6F_5$)B—, (vinyl)($C_6F_5$)B—, (benzyl)($C_6F_5$)B—, Cl($C_6F_5$)B—, ($CH_3O$)($C_6F_5$)B—, Cl($C_6F_5$)Al—, (alkyl)($C_6F_5$)Al—, ($C_6H_5$)($C_6F_5$)Al—, ($C_6F_5$)$_2$Al—, ($C_6F_5$)$_2$Ga— and ($C_6F_5$)(alkyl)Ga—.

Examples of substituents on the donor atoms N, P, As, Sb, Bi, O, S, Se or Te and on the acceptor atoms B, Al, Ga, In or Tl are $C_1$–$C_{12}$-(cyclo)alkyl such as methyl, ethyl, propyl, i-propyl, cyclopropyl, butyl, i-butyl, tert-butyl, cyclobutyl, pentyl, neopentyl, cyclopentyl, hexyl, cyclohexyl and the isomeric heptyls, octyls, nonyls, decyls, undecyls and dodecyls; the corresponding $C_1$–$C_{12}$-alkoxy groups; vinyl, butenyl and allyl; $C_6$–$C_{12}$-aryl such as phenyl, naphthyl or biphenylyl, and benzyl, which can be substituted by halogen, 1 or 2 $C_1$–$C_4$-alkyl groups, $C_1$–$C_4$-alkoxy groups, sulfonate, nitro or halogenoalkyl groups, $C_1$–$C_6$-alkylcarboxy, $C_1$–$C_6$-alkylcarbonyl or cyano (e.g. perfluorophenyl, m,m'-bis(trifluoromethyl)phenyl, tri($C_1$–$C_{20}$-alkyl)silyl, tri($C_6$–$C_{12}$-aryl)silyl and analogous substituents familiar to those skilled in the art); analogous aryloxy groups; indenyl; halogen such as F, Cl, Br and I; 1-thienyl; disubstituted amino such as ($C_1$–$C_{12}$-alkyl)$_2$ amino and diphenylamino; tris-($C_1$–$C_{12}$-alkyl)silyl; $NaSO_3$-aryl such as $NaSO_3$-phenyl and $NaSO_3$-tolyl; $C_6H_5$—C≡C—; aliphatic and aromatic $C_1$–$C_{20}$-Silyl whose alkyl substituents can be octyl, decyl, dodecyl, stearyl or eicosyl in addition to those mentioned above, and whose aryl substituents can be phenyl, tolyl, xylyl, naphthyl or biphenylyl; substituted silyl groups bonded to the donor atom or acceptor atom via —$CH_2$—, for example ($CH_3$)$_3$Si$CH_2$—; and ($C_1$–$C_{12}$-alkyl)(phenyl)amino, ($C_1$–$C_{12}$-alkylnaphthyl)amino, ($C_1$–$C_{12}$-alkylphenyl)$_2$-amino, $C_6$–$C_{12}$-aryloxy containing the above-mentioned aryl groups, $C_1$–$C_8$-perfluoroalkyl and perfluorophenyl. Preferred substituents are $C_1$–$C_6$-alkyl, $C_5$–$C_6$-cycloalkyl, phenyl, tolyl, $C_1$–$C_6$-alkoxy, $C_6$–$C_{12}$-aryloxy, vinyl, allyl, benzyl, perfluorophenyl, F, Cl, Br, di($C_1$–$C_6$-alkyl)amino and diphenylamino, although the acceptor atom carries at least one fluorinated aryl substituent and preferably two fluorinated aryl substituents.

Preferably all the substituents on the acceptor groups are fluorine-substituted aryl groups.

In this context, fluorinated means partially or completely fluorinated, the latter being preferred.

The acceptor group preferably contains an element of group XIII of the periodic table of the elements as defined by IUPAC, 1985.

Aryl is understood as meaning any of the mononuclear or polynuclear aryl radicals known to those skilled in the art, preferably the ones having 6 to 13 C atoms, such as phenyl, naphthyl, fluorenyl and indenyl, which in turn can be further substituted, although they have at least one fluorine substituent and preferably exclusively fluorine substituents. Fluorinated phenyl groups are preferred and perfluorinated phenyl groups are more preferred. In the case of partially fluorinated aryl groups, the remaining substituents, which can be identical or different, independently of one another are preferably selected from the group of hydrogen, $C_1$–$C_{20}$-alkyl such as methyl, ethyl, propyl, isopropyl, butyl or isobutyl, hexyl, octyl, decyl, dodecyl, hexadecyl, octadecyl and eicosyl, $C_1$–$C_{20}$-alkoxy such as methoxy, ethoxy, propoxy, isopropoxy, butoxy or isobutoxy, hexyloxy, octyloxy, decyloxy, dodecyloxy, hexadecyloxy, octadecyloxy and eicosyloxy, halogen such as chlorine or bromine, $C_6$–$C_{12}$-aryl such as phenyl, $C_1$–$C_4$-alkylphenyl such as tolyl, ethylphenyl, (i-)propylphenyl, (i-/tert-)butylphenyl and xylyl, halogenophenyl such as fluoro-, chloro- or bromophenyl, naphthyl or biphenylyl, triorganylsilyl such as trimethylsilyl (TMS), ferrocenyl, and D or A, as defined above.

Other possible donor and acceptor groups are those which contain chiral centers or in which 2 substituents form a ring with the D or A atom.

Express reference is made at this point to patent applications WO-A-98/01455, WO-A-98/145339, WO-A-98/101483 to WO-A-98/01487 and EP-A-1 041 086, which, for the purposes of US patent practice, are simultaneously included in the present patent application by way of reference.

The invention further relates to the use of the described transition metal compounds with a donor-acceptor interaction, characterized in that these transition metal compounds have a fluorine-substituted aryl group on at least one acceptor group, in a process for the homopolymerization or copolymerization of one or more olefins, i-olefins, alkynes or diolefins as monomers, or for ring-opening polyaddition, in the gas, solution, bulk, high-pressure or slurry phase, at −60 to +250° C., preferably up to +200° C., and 0.5 to 5000 bar, preferably 1 to 3000 bar, and in the presence or absence of saturated or aromatic hydrocarbons or saturated or aromatic halogeno-hydrocarbons, and in the presence or absence of hydrogen, these transition metal compounds with a donor-acceptor interaction being used in an amount ranging from $10^1$ to $10^{12}$ mol of all the monomers per mol of transition metal compound, and it also being possible for said process to be carried out in the presence of co-catalysts such as Lewis acids, Brönsted acids or Pearson acids, or additionally in the presence of Lewis bases.

Examples of such Lewis acids are boranes or alanes such as alkylaluminum compounds, aluminum halides, aluminum alcoholates, organoboron compounds, boron halides, boric acid esters or boron or aluminum compounds containing both halide and alkyl, aryl or alcoholate substituents, as well as mixtures thereof, or the triphenylmethyl cation. Aluminoxanes or mixtures of aluminum-containing Lewis acids with water are preferred. According to current knowledge, all acids work as ionizing agents to form a metallocenium cation which is charge-compensated by a bulky, poorly coordinating anion.

The invention further relates to the reaction products of such ionizing agents with compounds of general formula (I) or (II) according to the invention. They can be described by general formula (III) or (IV):

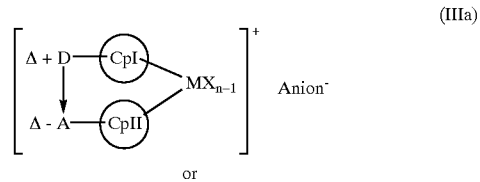

(IIIa)

or

-continued

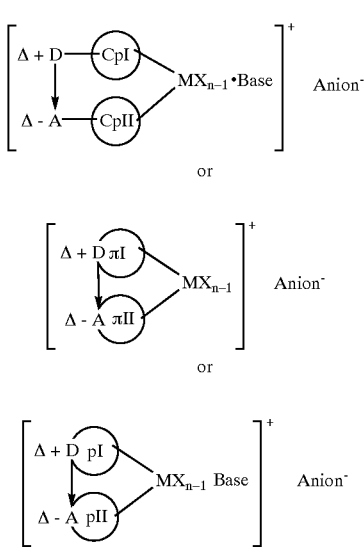

in which

Anion represents the whole of the bulky, poorly coordinating anion and Base represents a Lewis base.

The transition metal compounds of general formula (I), (II), (III) or (IV) according to the present invention can exist in either monomeric, dimeric or oligomeric form.

Examples of such poorly coordinating anions are $B(C_6H_5)_4^\ominus$, $B(C_6F_5)_4^\ominus$, $B(CH_3)(C_6F_5)_3^\ominus$,

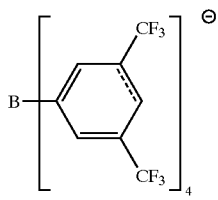

sulfonates such as tosylate or triflate, tetrafluoroborates, hexafluorophosphates, hexafluoroantimonates, perchlorates, bulky cluster molecular anions of the carborane type, for example $C_2B_9H_{12}^\ominus$ or $CB_{11}H_{12}^\ominus$, and substituted or unsubstituted cyclopentadienyl, indenyl and fluorenyl anions. Possible substituents are those already described for CpI and CpII. When such anions are present, π complex compounds can also work as highly efficient polymerization catalysts in the absence of aluminoxane. This is particularly the case when one X ligand is an alkyl group or benzyl. It can also be advantageous, however, to use such π complexes with bulky anions in combination with alkylaluminum compounds such as $(CH_3)_3Al$, $(C_2H_5)_3Al$, (n-/i-propyl)$_3Al$, (n-/t-butyl)3Al, (i-butyl)$_3Al$ or the isomeric pentyl-, hexyl- or octylaluminum compounds, alkyllithium compounds such as methyl-Li, benzyl-Li or butyl-Li, or the corresponding organomagnesium compounds, such as Grignard compounds, or organozinc compounds. On the one hand, such metal alkyls transfer alkyl groups to the central metal, and on the other hand they trap water or catalyst poisons from the reaction medium or monomer during polymerization reactions. The following are examples of aluminum or boron compounds from which such anions can be derived: triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl(2,4,6-trimethylanilinium) tetraphenylborate, trimethylammonium tetrakis (pentafluorophenyl)borate, triethylammonium tetrakis (pentafluorophenyl)borate, tripropylammonium tetrakis(pentafluorophenyl)borate, tri(n-butyl)ammonium tetrakis-(pentafluorophenyl)borate, tri(sec-butyl)ammonium tetrakis (pentafluorophenyl)borate, N,N-dimethylanilinium tetrakis (pentafluorophenyl)borate, N,N-diethylanilinium tetrakis (pentafluorophenyl)borate, N,N-dimethyl(2,4,5-trimethylanilinium) tetrakis(pentafluorophenyl)borate, trimethylammonium tetrakis(2,3,4,6-tetrafluorophenyl) borate, triethylammonium tetrakis(2,3,4,6-tetrafluorophenyl)borate, tripropylammonium tetrakis(2,3,4,6-tetrafluorophenyl)borate, tri(n-butyl)ammonium tetrakis (2,3,4,6-tetrafluorophenyl)borate, dimethyl(t-butyl) ammonium tetrakis(2,3,4,6-tetra-fluorophenyl)borate, N,N-dimethylanilinium tetrakis(2,3,4,6-tetrafluorophenyl)borate, N,N-diethylanilinium tetrakis(2,3,4,6-tetrafluorophenyl) borate and N,N-dimethyl(2,4,6-trimethylanilinium) tetrakis (2,3,4,6-tetrafluorophenyl)borate; dialkylammonium salts such as: di(i-propyl)ammonium tetrakis(pentafluorophenyl) borate and dicyclohexylammonium tetrakis (pentafluorophenyl)borate; trisubstituted phosphonium salts such as: triphenylphosphonium tetrakis(pentafluorophenyl) borate, tri(o-tolyl)phosphonium tetrakis(pentafluorophenyl) borate and tri(2,6-dimethylphenyl)phosphonium tetrakis (pentafluorophenyl)borate; tritolylmethyl tetrakis (pentafluoro-phenyl)borate; triphenylmethyl tetraphenylborate (trityl tetraphenylborate); trityl tetrakis (pentafluorophenyl)borate; silver tetrafluoroborate; tris (pentafluorophenyl)borane; tris(trifluoromethyl)borane; and the analogous aluminum compounds.

The transition metal compounds or metallocene compounds according to the present invention can be used in isolated form as pure substances for the (co)polymerization. However, they can also be produced and used "in situ" in the (co)polymerization reactor in a manner known to those skilled in the art.

Examples of other co-catalysts are aluminoxane compounds, which are understood as meaning compounds of formula (V):

in which

R is $C_1$–$C_{20}$-alkyl, $C_6$–$C_{12}$-aryl or benzyl and n is a number from 2 to 50, preferably 10 to 35.

It is also possible to use a mixture of different aluminoxanes or a mixture of their precursors (alkylaluminum compounds or alkylaluminum halides) in combination with water (in gaseous, liquid, solid or bound form, for instance as water of crystallization). The water can also be introduced as (residual) moisture in the polymerization medium, the monomer or a support like silica gel or aluminosilicate.

The bonds projecting from the square brackets of formula (V) carry R groups or $AlR_2$ groups as end groups of the oligomeric aluminoxane. Such aluminoxanes are normally present as a mixture of several with different chain lengths. Detailed study has also revealed aluminoxanes of cyclic or cage-like structure. Aluminoxanes are commercially available compounds. In the special case where $R=CH_3$, they are referred to as methylaluminoxanes (MAO).

The transition metal compound(s) and/or the co-catalyst (s) can be used either as such in homogeneous form or individually or together in heterogeneous form on supports. Such support can be of an inorganic or organic nature, such as silica gel, $B_2O_3$, $Al_2O_3$, $MgCl_2$, cellulose derivatives, starch and polymers, or else layered silicates like montmorillonites.

The supports are preferably thermally and/or chemically pretreated in order to adjust the water content or the OH group concentration to a defined value or keep it as low as possible. A chemical pretreatment can consist e.g. in reacting the support with alkylaluminum compound. Inorganic supports are usually heated at 100° C. to 1000° C. for 1 to 100 hours before use. The surface area of such inorganic supports, especially of silica ($SiO_2$), is between 10 and 1000 $m^2/g$, preferably between 100 and 800 $m^2/g$. The particle diameter is between 0.1 and 500 micrometers ($\mu$), preferably between 10 and 200$\mu$.

Examples of olefins, 1-olefins, cycloolefins, alkynes and diolefins to be reacted by homopolymerization or copolymerization are ethylene, propylene, 1-butene, i-butene, 1-pentene, 1-hexene, 1-octene, 3-methyl-1-butene, 4-methyl-1-pentene, 4-methyl-1-hexene, 1,3-butadiene, isoprene, 1,4-hexadiene, 1,5-hexadiene and 1,6-octadiene, methyloctadienes, chloroprene, acetylene and methylacetylene. α,ω-Diolefins afford the further possibility of a cyclizing polymerization, in which e.g. poly(methylene-1,3-cyclopentane) is formed from 1,5-hexadiene:

α,ω-Diolefins can also be used to produce long-chain branches.

If trialkylsilyl-substituted α,ω-diolefins are used, a functional group can subsequently be introduced by polymer-analogous reaction. The olefins and diolefins can also be substituted, for example by phenyl, substituted phenyl, halogen, an esterified carboxyl group or an acid anhydride group; examples of compounds of this type are styrene, methylstyrene, chlorostyrene, fluorostyrene, indene, 4-vinylbiphenyl, vinylfluorene, vinylanthracene, methyl methacrylate, ethyl acrylate, vinylsilane, trimethylallylsilane, vinyl chloride, vinylidene chloride, tetra-fluoroethylene, isobutylene, vinylcarbazole, vinylpyrrolidone, acrylonitrile, vinyl ethers, vinyl esters or vinylnorbornene.

Other possible processes according to the present invention are ring-opening polyadditions, for instance of lactones such as ε-caprolactone or δ-valerolactone, of lactams such as ε-caprolactam, of epoxides such as ethylene oxide or propylene oxide, or of other cyclic ethers such as tetrahydrofuran.

Cycloolefins which can be used are described in patent applications WO-98/01483 and WO-98/01484.

Preferred monomers are ethylene, propylene, butene, hexene, octene, 1,5-hexadiene, 1,6-octadiene, cycloolefins, methyl methacrylate, ε-caprolactone, δ-valerolactone and acetylene. It is possible to carry out said (co)polymerizations in the presence of hydrogen, for instance to adjust the molecular weight.

The homopolymerizations, copolymerizations or polyadditions to be carried out with the optionally supported transition metal compounds with a donor-acceptor interaction according to the present invention are performed under adiabatic or isothermal conditions in the indicated temperature and pressure ranges. This entails high-pressure processes in autoclaves or tubular reactors, solution processes, bulk polymerization processes, slurry phase processes in stirred reactors or loop reactors, and gas phase processes, the pressures for the slurry, solution and gas phases not exceeding 100 bar. Such polymerizations can also be carried out in the presence of hydrogen. All these processes have been known for a long time and are familiar to those skilled in the art.

Through the donor-acceptor bridge, the optionally supported transition metal compounds with a donor-acceptor interaction according to the present invention allow a defined opening of the two cyclopentadienyl skeletons or of the two ligands like a beak, thereby affording not only a high activity but also a high stereoselectivity, a controlled molecular weight distribution and a uniform incorporation of comonomers. A defined beak-like opening also creates room for bulky comonomers. A high uniformity of the molecular weight distribution is also a consequence of the uniform and defined site of the polymerization effected by insertion (single site catalyst).

The D/A structure can effect extra stabilization of the catalysts right up to high temperatures, so the catalysts can also be employed in the high temperature range from 80 to 250° C., preferably from 80 to 180° C. The possible thermal dissociation of the donor-acceptor bond is reversible and, through this self-organization process and self-repair mechanism, leads to particularly valuable catalyst properties. Thermal dissociation allows e.g. a specific broadening of the molecular weight distribution, facilitating the processability of the polymers. This effect also comes in useful e.g. in the case of catalysts in which the ligands, e.g. CpI and CpII, are linked together by both a covalent bridge and a D/A bridge. The D/A metallocene structures according to the present invention allow e.g. defect-free polyethylene formation to a degree not achieved with conventional catalysts. Accordingly, the ethylene polymers can have extremely high melting temperatures, for example above 135° C. to 160° C. (maximum of the DSC curve). Compared with the known polyethylenes, such high-melting polyethylenes have e.g. improved mechanical properties and thermostability (sterilizability in medical applications) and thereby, open up possible applications which hitherto seemed impossible for polyethylene and could only be achieved with e.g. high-tacticity polypropylene. Other characteristics are high enthalpies of fusion and high PE molecular weights. In particular, the catalysts according to the present invention afford interference-free growth of the polyethylene chains to give extremely high molecular weights.

Over a wide temperature range, although the PE molecular weight is lowered by raising the polymerization temperature, this occurs without a significant reduction in activity and by and large without going outside the range of high PE molecular weights and high PE melting temperatures which are of industrial value.

It has also been observed that transition metal compounds according to the invention with a donor-acceptor interaction of appropriate symmetry effect a regiospecific (isotactic, syndiotactic) polymerization of suitable monomers, but cause an increasingly unspecific (atactic) linking of the same monomer units in the upper part of said temperature range. This phenomenon has not yet been fully investigated, but it could be consistent with the observation that coordinate bonds which have an ionic bond superimposed on them, such as the donor-acceptor bonds in the metallocene compounds according to the invention, exhibit an increasing reversibility at elevated temperature. Thus, for example, it has been observed in the copolymerization of ethylene and propylene that, with the two comonomers present in equal proportions, a copolymer with a high propylene content is formed at low polymerization temperature, whereas the propylene content drops as the polymerization temperature increases until, ultimately, polymers containing predominantly ethylene are obtained at high temperature.

The reversible dissociation and association of the D/A structure and the mutual rotation of the ligands, for example of the Cp skeletons, which thereby becomes possible can be represented diagrammatically as follows:

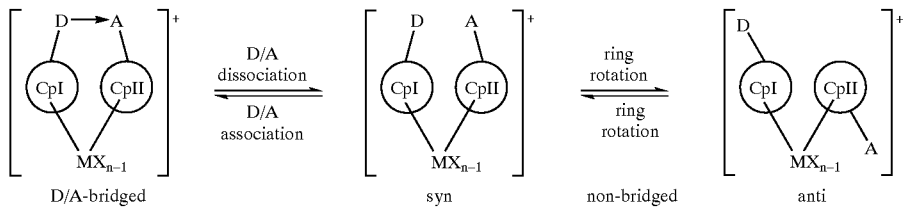

Another valuable property of the supported catalysts with a donor-acceptor interaction according to the present invention is the possibility of self-activation and hence of dispensing with expensive co-catalysts. Here, in the open form of the D/A metallocene compound, the acceptor atom A binds an X ligand to form a zwitterionic structure, thereby producing a positive charge on the transition metal, while the acceptor atom A assumes a negative charge. This kind of self-activation can take place intramolecularly or intermolecularly. This can be illustrated by considering the linking of two X ligands to a chelate ligand, i.e. the butadienediyl derivative:

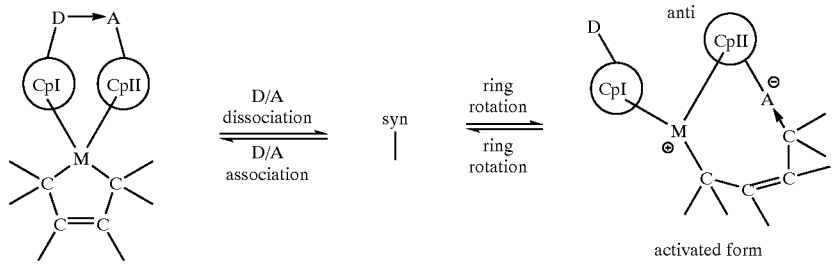

The binding site between the transition metal M and H or substituted or unsubstituted C, for instance the C which is still bound in the butadienediyl dianion shown in the exemplary formula, is then the olefin insertion site for polymerization.

The optionally supported transition metal compounds with a donor-acceptor interaction according to the present invention are also suitable for the preparation of both thermoplastic and elastomeric polymers by the various processes mentioned above, providing access both to highly crystalline polymers with an optimized melting range and to amorphous polymers with an optimized glass transition temperature. Also of particular interest are the polymers which can be prepared in this way and have a low glass transition temperature below 0° C. and a high melting temperature of >100° C. in one and the same material.

The polymers which can be prepared are outstandingly suitable for the production of all kinds of moldings, especially sheets, tubing, including that for medical purposes, profiles, disks, optical data storage media, cable sheathing, extrudates, surgical implants, ski running surface materials, impact strength modifiers for thermoplastics, for instance for car bumpers, etc.

The Examples which follow illustrate the invention.

EXAMPLES

All the reactions were carried out under strictly anaerobic conditions using Schlenk techniques or the high vacuum technique. The solvents used were dry ($LiAlH_4$ for pentane, hexane and heptane; sodium for toluene; sodium/benzophenone for diethyl ether; $CaH_2$ for methylene chloride) and saturated with argon. Chemical shifts $\delta$ are given in ppm relative to the appropriate standard: $^1H$ (tetramethylsilane), $^{13}C$ (tetramethylsilane), $^{19}F$ ($CCl_3F$), $^{31}P$ (85% $H_3PO_4$), $^{11}B$ (boron trifluoride etherate). Minus signs signify a shift to higher field.

Example 1

Dimethylbis(pentafluorophenyl)tin, $(CH_3)_2Sn(C_6F_5)_2$ (compound 1)

A two-neck round-bottom flask equipped with a condenser and a pressure-equalized dropping funnel, and containing Mg turnings (4.54 g, 187 mmol) and a stirrer bead, was dried thoroughly under vacuum, with heating. 200 ml of freshly distilled, sodium-dried diethyl ether and an iodine crystal were then introduced into the flask through a cannula. Bromopentafluorobenzene (dried over $CaH_2$ and freshly distilled, 46.12 g, 187 mmol) was introduced into the dropping funnel through a cannula and then added slowly to the Mg suspension so that the reaction mixture remained under gentle reflux during the addition. The mixture was refluxed for four hours and cooled to 0° C. A solution of dimethyltin dichloride, $Me_2SnCl_2$, (20.5 g, 93 mmol) in 150 ml of freshly distilled diethyl ether was then added over 30 min through a cannula. The reaction mixture was heated to room temperature and stirred overnight under argon. After the condenser had been replaced with a short-path distillation apparatus and the bulk of the diethyl ether had been distilled off, 200 ml of freshly distilled toluene were added. Distillation was continued until the diethyl ether had been completely removed from the reaction mixture. The toluene solution was filtered at room temperature under argon and the solid was washed with toluene (3×10 ml). The toluene was stripped from the combined filtrates under reduced pressure. The product was distilled under vacuum (3×10$^{-3}$ mbar, 110–140° C.) with cooling of the receiver flask. The end product was obtained in the form of a solid which was dense and colorless at room temperature (41.0 g, 90% yield).
$^1$H NMR (400.13 MHz, CD$_2$Cl$_2$), δ 0.83 (s, with $^{117}$Sn/$^{119}$Sn satellites).
$^{19}$F NMR (376.3 MHz, CD$_2$Cl$_2$), δ −122.0 (m, 4F, ortho), −151.7 (m, 2F, para), −160.7 (m, 4F, meta).
1). R. D. Chambers and T. Chivers. *J. Chem. Soc.* 1965, 3933.
2). D. J. Parks, R. E. H. Spence and W. E. Piers, *Angew. Chem.* 1995, 107, 895.
3). R. E. H. Spence, D. J. Parks, W. E. Piers, M.-A. MacDonald, M. J. Zawarotko and S. J. Rettig, *Angew. Chem.* 1995, 107, 1337.

Example 2

Bis(pentafluorophenyl)boron Chloride, (C$_6$F$_5$)$_2$BCl (compound 2)

A solution of dimethylbis(pentafluorophenyl)tin, Me$_2$Sn(C$_6$F$_5$)$_2$, (40.98 g, 84.9 mmol) in 30 ml of dry heptane was placed in a thoroughly dried 500 ml Schlenk tube equipped with a side-arm with a J-Young stopcock, a Teflon/rubber double 0-ring stopper and a stirrer bead. The solution was cooled to −70° C. and a solution of BCl$_3$ (85 ml of a 1.0 M solution in heptane, 85 mmol) was added via a syringe. The Schlenk tube was tightly sealed and the solution was allowed to warm up slowly to room temperature and stirred for 2.5 hours at RT, during which time some precipitation occurred. The Schlenk tube was then heated for 30 hours in an oil bath at 105° C. Some crystals may condense in the top part of the tube during this process. The reaction mixture was allowed to cool slowly to room temperature overnight, a large amount of Me$_2$SnCl$_2$ crystals precipitating out of the solution. The supernatant was transferred by means of a cannula to another thoroughly dried flask, after which the crystals were washed with hexane (2×20 ml), the hexane being combined with the supernatant. By drying the crystals, pure Me$_2$SnCl$_2$ was more than 90% recovered. After the volatile components had been stripped from the solution under reduced pressure, the off-white solid was briefly dried under vacuum to give 31.3 g of crude product, which was redissolved in the minimum volume of hexane. After filtration of the insoluble components (principally Me$_2$SnCl$_2$), the clear solution was cooled at −30° C. overnight. The supernatant was removed through a cannula while the solution was still cold, and the crystals were dried under vacuum to give the pure compound, ClB(C$_6$F$_5$)$_2$, (26.42 g, 82%) in the form of extremely air-sensitive and moisture-sensitive crystals.
$^{11}$B NMR (80.25 MHz, CD$_2$Cl$_2$), δ 58.0 (br. s).
$^{19}$F NMR (376.3 MHz, CD$_2$Cl$_2$), δ −129.5 (m, 4F, ortho), −145.5 (m, 2F, para), −161.6 (m, 4F, meta).
1.a). R. Duchateau, S. J. Lancaster, M. Thornton-Pett and M. Bochmann. *Organometallics* 1997, 16, 4995. b). M. Bochmann, S. J. Lancaster and O. B. Robinson. *J. Chem. Soc. Chem. Commun.* 1995, 2081.
2.a). R. D. Chambers and T. Chivers. *J. Chem. Soc.* 1965, 3933. b). D. J. Parks, R. E. H. Spence and W. E. Piers. *Angew. Chem.* 1995, 107, 895. c). R. E. H. Spence, D. J. Parks, W. E. Piers, M.-A. MacDonald, M. J. Zawarotko and S. J. Rettig. *Angew. Chem.* 1995, 107, 1337.
3. S. J. Lancaster, M. Thornton-Pett, D. M. Dowson and M. Bochmann. *Organometallics* 1998, 17, 3829.

Example 3

1-Trimethylstannyl-2-methylindene, (CH$_3$)$_3$Sn(C$_9$H$_6$)CH$_3$ (compound 3)

BuLi (48 ml of a 2.5 molar solution in hexane, 120.0 mmol) was added at −70° C. by means of a syringe to a solution of 2-methylindene (14.62 g, 112.3 mmol) in 400 ml of hexane, after which the mixture was stirred under argon and allowed to warm up slowly to room temperature overnight. After the volatile components had been separated off by filtration through a cannula, the white solid was washed with hexane (3×50 ml) to remove excess BuLi. The solid was then suspended in 300 ml of hexane, and a solution of chlorotrimethyltin, Me$_3$SnCl, (22.40 g, 112.4 mmol) in 100 ml of hexane was added at 0° C. through a cannula. The resulting mixture was refluxed for 2.5 hours and stirred for 16 hours at room temperature. The white precipitate was filtered off and volatile components were removed from the filtrate under reduced pressure. The oily residue was distilled under reduced pressure to give 31.35 g of a yellow oil (95% crude yield). The product is pure according to $^1$H NMR spectroscopy.
NMR:
$^1$H (400.13 MHz, C$_6$D$_6$), δ 7.44 (d, J=7.5 Hz, 1H), 7.28 (d, J=7.5 Hz, 1H), 7.21 (t, J=6.7 Hz, 1H), 7.13 (t, J=6.6Hz, 1H), 6.49 (s, 1H), 3.55 (s, 1H), 1.99 (s, 3H), −0.11 (s, 9H).
$^{13}$C (100.6 MHz, C$_6$D$_6$), δ 146.7, 145.7, 143.6, 124.3, 122.6, 122.4, 121.4, 120.3, 47.6, 16.7, −9.8.

Example 4

Bis(trimethylstannyl)-2-methylindene, {(CH$_3$)$_3$Sn}$_2$(C$_9$H$_5$)CH$_3$ (compound 4)

Dimethylaminotrimethyltin, Me$_3$SnNMe$_2$, (13.9 g, 66.9 mmol) was added at room temperature to 1-trimethylstannyl-2-methylindene, (CH$_3$)$_3$Sn(C$_9$H$_6$)CH$_3$, (17.0 g, 58.0 mmol) by means of a syringe, after which the mixture was heated in an oil bath for 12 h at 105–110° C. and stirred for a further 16 h at room temperature. After volatile components had been stripped off under vacuum, short-path distillation of the oily residue gave 26.37 g (99.7% yield) of a pale yellow oil, which solidifies slowly at room temperature. The product is pure title compound according to $^1$H NMR spectroscopy.
NMR:
$^1$H (400.13 MHz, C$_6$D$_6$), δ 7.55 (d, J=7.4 Hz, 1H), 7.43 (d, J=7.4 Hz, 1H), 7.21 (t, J=7.4, 1H), 7.15 (t, J=7.6, 1H), 6.70 (s, 1H), 2.12 (s, 3H), 0.0 (s, 9H).
$^{13}$C (100.6 MHz, C$_6$D$_6$), δ 149.6, 149.1, 143.4, 123.3, 122.3, 122.1, 121.4, 120.3, 17.7, −8.5.

Example 5

2-Methyl-4-phenylindenyllithium, Li[2-CH$_3$-4-C$_6$H$_5$—(C$_9$H$_5$)] (compound 5)

BuLi (65.2 ml of a 2.5 molar solution in hexane, 0.163 mol) was added at −70° C. over 10 min by means of a syringe to a solution of 2-methyl-4-phenylindene [1] (33.58 g, 0.163 mol) in 350 ml of dry hexane.

The mixture was allowed to warm up slowly to room temperature overnight under an Ar atmosphere. The pale yellow suspension was filtered and the solid was washed with hexane (2×60 ml) and dried to constant weight under high vacuum. The product was obtained in the form of a loose, pale yellow powder (31.04 g, 90%).
$^1$H NMR (400.13 MHz, THF-d$_8$), δ 7.80 (dd, J$_1$=8.2 Hz, J$_2$=1.4 Hz, 2H), 7.28 (t, J=7.6 Hz, 2H), 7.16 (d, J=7.5 Hz, 1H), 7.10 (t, J=7.3 Hz, 1H), 6.49 (m, 2H), 6.01 (s, 1H), 5.81 (s, 1H), 2.36 (s, 3H).

[1]. W. Spaleck, F. Küber, A. Winter, J. Rohrmann, B. Bachmann, M. Antberg, V. Dolle and E. F. Paulus. *Organometallics* 1994, 13, 954.

Example 6

Bis(trimethylstannyl)-2-methyl-4-phenylindene, $\{(CH_3)_3Sn\}_2$-2-$CH_3$-4-$C_6H_5$—$(C_9H_5)$ (compound 6)

A solution of chlorotrimethyltin, $ClSnMe_3$, (17.82 g, 89.4 mmol) in 60 ml of dry hexane was added at −70° C. over 15 min through a cannula to a suspension of 2-methyl-4-phenylindenyllithium, Li[2-Me-4-Ph-$(C_9H_5)$], (18.98 g, 89.4 mmol) in 200 ml of dry hexane. The mixture was allowed to warm up slowly to room temperature overnight. The white suspension was filtered over Célite to separate off LiCl, and all the volatile components were removed from the filtrate under reduced pressure. The residual oil was kept under vacuum for 15 min to leave 32.34 g (98%) of a viscous oil, which was pure according to $^1$H NMR. The product was dissolved in an equivalent amount of trimethyltin dimethylamide, $Me_2N$—$SnMe_3$, (18.22 g, 87.6 mmol). After the mixture had been heated in an oil bath for 20 hours at 110° C., minor volatile components were removed from the highly viscous liquid under vacuum. The residue solidified slowly at room temperature to give 45.07 g (96.7%) of an olive-green solid, which was pure according to $^1$H NMR spectroscopy.

$^1$H NMR (400.13 MHz, $CD_2Cl_2$), δ 7.64 (m, 2H), 7.49 (t, J=7.4 Hz, 2H), 7.27 (m, 2H), 7.18 (m, 2H), 6.88 (s, 1H), 2.28 (s, 3H), 0.13 (s, 18H).

Example 7

Fluorenyllithium, Li($C_{13}H_9$) (compound 7)

BuLi (28.0 ml of a 2.5 molar solution, 70.0 mmol) was added at −70° C. to a solution of fluorene (11.09 g, 66.74 mmol) in 300 ml of dry pentane. The resulting pale yellow solution was stirred at room temperature for 16 hours under an Ar atmosphere and then refluxed for 24 hours. The orange-yellow solution was filtered through a cannula and the yellow solid residue was washed with pentane (2×100 ml, each time for approx. 15 min under reflux) and filtered off. The orange-yellow powder was dried to constant weight under a dynamic vacuum to give 9.10 g (79.2%) of pure product, fluorenyllithium, in the form of a loose, orange-colored powder.

$^1$H NMR (400.13 MHz, THF-$d_8$), δ 7.86 (d, J=7.53 Hz, 2H), 7.25 (d, J=7.96 Hz, 2H), 6.75 (td, $J_1$=6.65 Hz, $J_2$=1.22 Hz, 2H), 6.37 (t, J=7.64 Hz, 2H), 5.88 (s, 1H).

1). J. B. Grutzner et al. *J. Amer. Chem. Soc.* (1972), 94, 2306.
2). J. J. Brooks et al. *J. Amer. Chem. Soc.* (1972), 94, 7339.
3). R. Zerger et al. *J. Amer. Chem. Soc.* (1974), 96, 5441.

Example 8

Trimethylsilyldimethylphosphinocyclopentadiene, $(CH_3)_3Si(C_5H_4)P(CH_3)_2$ (compound 8)

A solution of chlorodimethylphosphine, $ClPMe_2$, (5.32 g, 54.0 mmol) in 20 ml of hexane was added at −70° C. over 15 min through a cannula to a suspension of lithium trimethylsilylcyclopentadienide, Li($C_5H_4$)$SiMe_3$, (7.82 g, 54.2 mmol) in 100 ml of hexane. The mixture was allowed to warm up slowly to room temperature overnight under an Ar atmosphere, with stirring. After filtration of the suspension over Célite to separate off LiCl, volatile components were removed from the filtrate under reduced pressure to give 10.2 g (95%) of an oily yellow residue as crude product, which is pure according to $^1$H and $^{31}$P NMR spectroscopy. Short-path distillation of the crude product gave a light yellow oil (9.33 g, 87%). The $^1$H and $^{31}$P NMR spectra indicate a complicated mixture of isomers.

Example 9

Trimethylsilyldiethylphosphinocyclopentadiene, $(CH_3)_3Si(C_5H_4)P(C_2H_5)_2$ (compound 9)

A solution of chlorodiethylphosphine, $ClP(CH_2CH_3)_2$, (4.87 g, 39.1 mmol) in 50 ml of hexane was added at −70° C. over 25 min through a cannula to a suspension of lithium trimethylsilylcyclopentadienide, Li($C_5H_4$)$SiMe_3$, (5.8 g, 40 mmol) in 100 ml of hexane. The resulting suspension was stirred under an Ar atmosphere and allowed to warm up slowly to room temperature overnight. After filtration of the suspension over Célite, volatile components were removed from the filtrate to give a light yellow oil (7.53 g, 83%), which was redistilled under reduced pressure to give an isomer mixture in the form of a pale yellow oil (6.96 g, 78.6%), 1-trimethylsilyl-3-diethylphosphinocyclopentadiene being the main product.

Example 10

Trimethylsilyldiisopropylphosphinocyclopentadiene, $(CH_3)_3Si(C_5H_4)P\{CH(CH_3)_2\}_2$ (compound 10)

A solution of trimethylchlorosilane, $Me_3SiCl$, (2.5 g, 23 mmol) in 40 ml of hexane was added at −70° C. over 25 min through a cannula to a solution of lithium diisopropylphosphinocyclopentadienide, Li($C_5H_4$)P($CHMe_2$)$_2$, (4.32 g, 23 mmol) in 60 ml of hexane. The mixture was stirred overnight under an Ar atmosphere. After filtration of the resulting suspension to separate off LiCl, volatile components were removed from the filtrate under reduced pressure to leave a crude product in the form of an orange-colored oil (3.28 g, 56%). The crude product was distilled under vacuum (>80° C./3.5×10$^{-3}$ mbar) to give a mixture of positional isomers in the form of a light yellow oil (2.01 g).

Example 11

Trimethylsilyldiphenylphosphinocyclopentadiene, $(CH_3)_3Si(C_5H_4)P(C_6H_5)_2$ (compound 11)

A solution of chlorodiphenylphosphine, $ClP(C_6H_5)_2$, (8.8 g, 40.15 mmol) in 50 ml of hexane was added at −70° C. over 15 min through a cannula to a suspension of lithium trimethylsilylcyclopentadienide, Li($C_5H_4$)$SiMe_3$, (5.79 g, 40.15 mmol) in 100 ml of hexane. The mixture was allowed to warm up slowly to room temperature overnight. The orange-colored suspension was filtered through a no. 3 frit and the solid was washed with $CH_2Cl_{12}$ (2×30 ml). The volatile components were stripped from the filtrate under reduced pressure to leave a thick, oily, dark brown residue, which was distilled under high vacuum (200° C./3.3×10$^{-3}$ mbar) to give a viscous yellow liquid (11.62 g, 90%). The distilled product was kept under vacuum for a further 2 hours at room temperature to remove residual traces of chlorodiphenylphosphine. The $^1$H and $^{31}$P NMR spectra indicate a complicated isomer mixture.

Example 12

Dimethylphosphino-2-methyl-4-phenylindenyllithium, Li[$(CH_3)_2$P-2-$CH_3$-4-$(C_6H_5)$—$(C_9H_4)$] (compound 12)

A solution of chlorodimethylphosphine, $ClPMe_2$, (1.464 g, 15.2 mmol) in 15 ml of dry pentane was added at −70° C.

over 10 min through a cannula to a suspension of 2-methyl-4-phenylindenyllithium, Li[2-Me-4-Ph-($C_9H_5$)], (3.22 g, 15.2 mmol) in 30 ml of dry pentane. The mixture was allowed to warm up slowly to room temperature overnight. The suspension was then filtered over Célite and volatile components were removed under reduced pressure to leave 3.16 g (78%) of a yellow oil, which was dimethylphosphino-2-methyl-4-phenylindene according to $^1$H and $^{31}$P NMR spectroscopy. The product (3.16 g, 11.87 mmol) was diluted in 50 ml of dry pentane and cooled to −70° C. BuLi (4.80 ml of a 2.5 molar solution in hexane, 12.0 mmol) was added to the cold solution by means of a syringe. The mixture was allowed to warm up slowly to room temperature and stirred overnight. The resulting yellow suspension was filtered through a cannula and the solid residue was washed with pentane (3×15 ml) to leave 3.02 g (93.5%) of a loose yellow solid, which was the title compound, dimethylphosphino-2-methyl-4-phenylindenyllithium, according to $^1$H and $^{31}$P NMR spectroscopy.

NMR for the end product, 1-dimethylphosphino-2-methyl-4-phenylindenyllithium (main isomer):
$^1$H (400.13 MHz, THF-$d_8$), δ 7.73 (dd, $J_1$=8.2 Hz, $J_2$=1.3 Hz, 2H), 7.53 (d, J=7.4 Hz, 1H), 7.21 (t, J=7.8 Hz, 2H), 7.02 (t, J=7.4 Hz, 1H), 6.39 (m, 2H), 6.00 (d, J=3.9 Hz, 1H), 2.46 (s, 3H), 1.38 (d, J=3.6 Hz, 6H).
$^{31}$P (161.9 MHz, THF-$d_8$), δ −73.0 ppm.

Example 13

Diethylphosphino-2-methyl-4-phenylindenyllithium, Li[($C_2H_5$)$_2$P-2-$CH_3$-4-$C_6H_5$—($C_9H_4$)] (compound 13)

A solution of chlorodiethylphosphine, ClPEt$_2$, (0.981 g, 7.88 mmol) in 15 ml of pentane was added at −70° C. through a cannula to a suspension of 2-methyl-4-phenylindenyllithium, Li[2-Me-4-Ph-($C_9H_5$)], (1.672 g, 7.88 mmol) in 20 ml of dry pentane. The mixture was allowed to warm up slowly to room temperature overnight. The yellow suspension was filtered over Célite and volatile components were removed under reduced pressure to leave 2.28 g (98%) of a pale yellow oil, which was diethylphosphino-2-methyl-4-phenylindene according to $^1$H and $^{31}$P NMR spectroscopy. The product obtained above (2.28 g, 7.75 mmol) was diluted in 35 ml of dry pentane and cooled to −70° C. BuLi (3.2 ml of a 2.5 molar solution in hexane, 8.0 mmol) was then added to the solution. The mixture was slowly warmed up to room temperature and stirred overnight. The pale yellow suspension was filtered through a cannula and the remaining solid was washed with pentane (3×10 ml) and dried under vacuum to give 1.90 g (81.7%) of a yellow powder, which was the title compound according to $^1$H and $^{31}$P NMR spectroscopy. Main isomer: diethylphosphino-2-methyl-4-phenylindenyllithium.
NMR:
$^1$H (400.13 MHz, THF-$d_8$), δ 7.82 (d, J=7.6 Hz, 2H), 7.53 (d, J=7.5 Hz, 1H), 7.28 (t, J=7.6 Hz, 2H), 7.09 (t, J=7.2 Hz, 1H), 6.45 (m, 2H), 6.12 (d, J=3.6 Hz, 1H), 2.53 (s, 3H), 2.01 (m, 2H), 1.82 (m, 2H), 1.01 (t, J=7.6 Hz, 3H), 0.97 (t, J=7.7 Hz, 3H).
$^{31}$P (161.9 MHz, THF-$d_8$), δ −36.0 ppm (singlet).

Example 14

Trimethylstannyl-2-methyldiethylphosphino-4-phenylindene, ($CH_3$)$_3$Sn-2-$CH_3$-3-($C_2H_5$)$_2$P-4-$C_6H_5$—($C_9H_4$) (compound 14)

Diethylphosphino-2-methyl-4-phenylindenyllithium (6.62 mmol) was suspended in 30 ml of hexane and cooled to −70° C. and a solution of chlorotrimethyltin, ClSnMe$_3$, (1.32 g, 6.62 mmol) in 15 ml of hexane was then added. The mixture was warmed up to room temperature and stirred for a further 3 hours. The suspension was then filtered over Célite and volatile components were removed under reduced pressure. The viscous oil was kept under vacuum for a further 15 min to give 2.72 g (90%) of the title compound, Me$_3$Sn-2-Me-Et$_2$P-4-Ph-($C_9H_4$), in the form of a yellowish-brown oil.

Example 15

9-Dimethylphosphinofluorenyllithium, Li[9-($CH_3$)$_2$P-($C_{13}H_8$)] (compound 15)

A solution of chlorodimethylphosphine, ClPMe$_2$, (1.0 g, 10.39 mmol) in 20 ml of pentane was added at −70° C. over 10 min through a cannula to a suspension of fluorenyllithium, ($C_{13}H_9$)Li, (1.788 g, 10.39 mmol) in 30 ml of dry pentane. After brief stirring at −70° C., the cooling bath was removed and the mixture was stirred for 4 hours at room temperature under an Ar atmosphere (with occasional heating by means of a hairdryer). 20 ml of toluene were added to the suspension to assist the dissolution of the product. The pale yellow suspension was filtered and volatile components were removed from the filtrate under vacuum to leave 2.34 g (99.6%) of 9-dimethylphosphinofluorene in the form of a pale yellow oil, which is pure according to $^1$H and $^{31}$P NMR. The product, 9-dimethylphosphinofluorene, (2.34 g, 10.34 mmol) was diluted in 25 ml of pentane and cooled to −70° C. BuLi (4.20 ml of a 2.5 molar solution, 10.5 mmol) was added to the cooled solution and the mixture was stirred briefly at −70° C. and then at room temperature. The clear yellow solution slowly becomes turbid at room temperature and a yellow precipitate begins to form. After a reaction time of 5 hours at room temperature, the mixture was filtered through a cannula and the yellow solid was washed with dry pentane (3×5 ml) and dried under high vacuum to leave 1.91 g (80%) of a loose orange-yellow solid, which is the title compound, 9-dimethylphosphinofluorenyllithium, according to $^1$H and $^{31}$P NMR spectroscopy.
NMR:
$^1$H (400.13 MHz, THF-$d_8$), δ 7.81 (d, J=7.8 Hz, 2H), 7.71 (d, J=8.2 Hz, 2H), 6.80 (t, J=7.8 Hz, 2H), 6.44 (t, J=7.3 Hz, 2H), 1.44 (d, J=3.4 Hz, 6H).
$^{31}$P (161.9 MHz, THF-$d_8$), δ −76.7 (singlet).

Example 16

9-Diethylphosphinofluorenyllithium, Li[9-($C_2H_5$)$_2$P-($C_{13}H_8$)] (compound 16)

A solution of chlorodiethylphosphine, ClPEt$_2$, (1.974 g, 15.85 mmol) in 25 ml of pentane was added at −70° C. to a suspension of fluorenyllithium, ($C_{13}H_9$)Li, (2.728 g, 15.85 mmol) in 30 ml of dry pentane. The mixture was stirred briefly at −70° C. and then reacted for 6 hours at room temperature. The yellow suspension was filtered and volatile components were removed from the filtrate under vacuum to leave 3.49 g (86.6%) of an orange-colored oil, which was 9-diethylphosphinofluorene according to $^1$H and $^{31}$P NMR spectroscopy. The compound obtained above (9-diethylphosphinofluorene, 3.388 g, 13.3 mmol) was diluted in 45 ml of dry pentane and cooled to −70° C. BuLi (5.4 ml of a 2.5 molar solution, 13.5 mmol) was added to the cooled solution and the mixture was stirred briefly. It was stirred for a further 4.5 hours at room temperature, with occasional heating by means of a hairdryer, to form a loose orange-colored precipitate. The reaction mixture was filtered through a cannula and the solid was washed with pentane (2×5 ml) and dried under vacuum to leave an orange-colored solid, which was 9-diethylphosphinofluorenyllithium according to $^1$H and $^{31}$P NMR spectroscopy.

NMR:
$^1$H (400.13 MHz, THF-d$_8$), δ 7.79 (d, J=7.5 Hz, 2H), 7.68 (d, J=8.2 Hz, 2H), 6.76 (dt, J$_1$=6.8 Hz, J$_2$=1.3 Hz, 2H), 6.41 (dt, J$_1$=6.8 Hz, J$_2$=0.8 Hz, 2H), 2.08 (m, 2H), 1.82 (m, 2H), 0.90 (m, 6H).
$^{31}$P (161.9 MHz, THF-d$_8$), δ −40.4 (singlet).

Example 17

9-Diisopropylphosphinofluorenyllithium, Li[9{(CH$_3$)$_2$CH}$_2$P-(C$_{13}$H$_8$)] (compound 17)

A solution of chlorodiisopropylphosphine, ClP(i-Pr)$_2$, (1.503 g, 9.85 mmol) in 15 ml of dry pentane was added at −70° C. over 15 min through a cannula to a suspension of fluorenyllithium, Li(C$_{13}$H$_9$), (1.696 g, 9.85 mmol) in 30 ml of dry pentane. The orange-colored suspension was allowed to warm up slowly to room temperature and stirred overnight. The yellow suspension was then filtered over Célite and volatile components were removed from the filtrate under vacuum to give 2.68 g (96.5%) of a viscous orange-colored oil, which was 9-diisopropylphosphinofluorene according to $^1$H and $^{31}$P NMR spectroscopy. The product, 9-diisopropylphosphinofluorene, (2.68 g, 9.49 mmol) was diluted in 50 ml of dry pentane and cooled to −70° C. and BuLi (4.0 ml of a 2.5 molar solution, 10.0 mmol) was added. The mixture was allowed to warm up slowly to room temperature overnight under an Ar atmosphere. The orange-colored suspension was filtered through a cannula and the solid was washed with dry pentane (2×15 ml) and dried under high vacuum to give 2.58 g (94%) of an orange-colored powder, which was the title compound, 9-diisopropylphosphinofluorenyllithium, according to $^1$H and $^{31}$P NMR spectroscopy.

NMR:
$^1$H (400.13 MHz, THF-d$_8$), δ 7.85 (d, J=7.5 Hz, 2H), 7.75 (d, J=7.9 Hz, 2H), 6.83 (dt, J$_1$=7.8 Hz, J$_2$=1.1 Hz, 2H), 6.47 (t, J=7.5 Hz, 2H), 2.63 (m, 2H), 1.15 (dd, J$_1$=15.2 Hz, J$_2$=6.9 Hz, 6H), 0.92 (dd, J$_1$=10.4 Hz, J$_2$=6.9 Hz, 6H).
$^{31}$P (161.9 MHz, THF-d$_8$), δ −6.57 ppm (singlet).

Example 18

Trimethylsilylbis(pentafluorophenyl)boranylcyclopentadiene, (CH$_3$)$_3$Si(C$_5$H$_4$)B(C$_6$F$_5$)$_2$ (compound 18)

A solution of chlorobis(pentafluorophenyl)borane, ClB(C$_6$F$_5$)$_2$, (11.09 g, 29.1 mmol) in 50 ml of hexane was added at −70° C. over 15 min to a suspension of Me$_3$Si(C$_5$H$_4$)Li (4.20 g, 29.1 mmol) in 25 ml of hexane. The mixture was allowed to warm up slowly to room temperature overnight, with stirring. After filtration of the yellow suspension, the solid was washed with hexane (2×5 ml). The volatile components were stripped from the filtrate under reduced pressure to leave a yellowish-brown gummy liquid, which slowly crystallized over a few days at room temperature to give yellowish-brown crystals (13.6 g, approx. 97%).
$^1$H NMR (400.13 MHz, CD$_2$Cl$_2$), δ for main isomer: 7.61 (br., 1H), 7.10 (br., 1H), 7.00 (br., 1H), 4.9 (br., 1H), 0.00 (s, 9H).
$^{11}$B NMR (80.25 MHz, CD$_2$Cl$_2$), δ 53.0 (br. s).
$^{19}$F NMR (376.3 MHz, CD$_2$Cl$_2$), δ −130.6 (m, 4F), −152.0 (m, 2F), −162.6 (m, 4F).

1.a). R. Duchateau, S. J. Lancaster, M. Thornton-Pett and M. Bochmann. *Organometallics* 1997, 16, 4995. b). M. Bochmann, S. J. Lancaster and O. B. Robinson. *J. Chem. Soc. Chem. Commun.* 1995, 2081.
2. S. J. Lancaster, M. Thornton-Pett, D. M. Dowson and M. Bochmann. *Organometallics* 1998, 17, 3829.

Example 19

Trimethylstannyl-2-methylbis(pentafluorophenyl)boranylindene, (CH$_3$)$_3$Sn-2-CH$_3$—(C$_9$H$_5$)B(C$_6$F$_5$)$_2$ (compound 19)

A solution of bis(trimethylstannyl)-2-methylindene, (Me$_3$Sn)$_2$-2-Me-(C$_9$H$_5$), (3.29 g, 7.23 mmol) in 30 ml of pentane was cooled to −70° C. and a solution of bis(pentafluorophenyl)boron chloride, ClB(C$_6$F$_5$)$_2$, (2.75 g, 7.23 mmol) in 30 ml of pentane was added dropwise over 20 min through a cannula. A bright yellow slurry formed immediately. The mixture was kept at −70° C. for 2 hours and allowed to warm up slowly to 12° C. overnight (14 hours). After the volatile components had been stripped from the yellow slurry, the residue was kept at 2.5×10$^{-3}$ mbar for 5 hours to remove Me$_3$SnCl by sublimation. The residue was taken up in 30 ml of pentane, redissolved and stored overnight in a freezing cabinet at −30° C. The bright yellow crystals were filtered off and washed with cold pentane to give 1.36 g of product (29.5%) in pure form. A second fraction of 1.01 g (21.9%) was isolated from the concentrated cold mother liquor (51% in total). Both fractions are spectroscopically pure.

NMR:
$^1$H (400.13 MHz, CD$_2$Cl$_2$), δ 7.38 (d, J=7.6 Hz, 1H), 7.17 (t, J=7.3 Hz, 1H), 7.05 (t, J=7.1 Hz, 1H), 6.99 (d, J=7.8 Hz, 1H), 4.85 (s, with Sn satellites due to coupling via two bonds, 1H), 2.26 (s, 3H), 0.18 (s, 9H).
$^{11}$B (128.4 MHz, CD$_2$Cl$_2$), δ 54.1.
$^{13}$C (100.58 MHz, CD$_2$Cl$_2$), δ 177.9, 146.2 (md, $^1$J$_{C-F}$=240.5 Hz), 144.4, 142.8, 142.6 (md, $^1$J$_{C-F}$=254.7 Hz), 138.2 (md, $^1$J$_{C-F}$=269.7 Hz), 124.6, 123.9, 121.2, 120.6, 63.7, 19.1, −7.5.
$^{19}$F (376.3 MHz, CD$_2$Cl$_2$), δ −132.1 (dd, J$_1$=23 Hz, J$_2$=9 Hz, o-F), −153.0 (t, J=20 Hz, p-F), −162.4 (dt, J$_1$=20 Hz, J$_2$=9 Hz, m-F).

Example 20

Bis(pentafluorophenyl)boranyl-2-methyltrimethylstannyl-4-phenylindene, [(F$_5$C$_6$)$_2$B-2-CH$_3$-4-C$_6$H$_5$(C$_9$H$_4$)-Sn(CH$_3$)$_3$] (compound 20)

A solution of bis(pentafluorophenyl)boron chloride, ClB(C$_6$F$_5$)$_2$, (5.026 g, 13.2 mmol) in 20 ml of dry pentane was added at −70° C. over 30 min through a cannula to a suspension of bis(trimethylstannyl)-2-methyl-4-phenylindene, (Me$_3$Sn)$_2$-2-Me-4-Ph-(C$_9$H$_4$), (7.028 g, 13.2 mmol) in 40 ml of dry pentane. The mixture (a pale yellow slurry) was stirred at −70° C. for 260 min and then warmed up to −30° C. over 35 min. The volatile components were then stripped off under vacuum, the temperature being kept below −30° C. The by-product, trimethyltin chloride, was removed from the resulting yellow paste by treatment under vacuum for 6 hours to give 8.72 g (92.6%) of crude product in the form of a sticky yellow solid.

Example 21

Bis(pentafluorophenyl)boranylcyclopentadienylzirconium Trichloride, (C$_6$F$_5$)$_2$B(C$_5$H$_4$)ZrCl$_3$ (compound 21)

A solution of trimethylsilylbis(pentafluorophenyl)-boranylcyclopentadiene, Me$_3$Si(C$_5$H$_4$)B(C$_6$F$_5$)$_2$, (4.0 g, 8.25 mmol) in 60 ml of toluene was added at room temperature to a suspension of $ZrCl_4$ (1.92 g, 8.24 mmol) in 30 ml of toluene. The mixture was stirred overnight (16 h) under Ar. After filtration of the suspension, the light yellow solid was washed with toluene (2×5 ml) and the loose solid was dried to constant weight under a vacuum of $3 \times 10^{-3}$ mbar (3.88 g, 77.6%).
NMR:
$^1$H (400.13 MHz, $d_8$-toluene), δ 6.87 (br. s), 6.51 (br. s), 6.46 (t, J=2.5 Hz), 6.28 (t, J=2.6 Hz).
$^{11}$B (128.4 MHz, $d_8$-toluene), δ 54.3 (broad signal at 65–45 ppm with maximum at 54.3 ppm).
$^{19}$F (376.3 MHz, $d_8$-toluene), δ −127.3 (br. s), −128.4 (d, J=19.9 Hz), −146.1 (br. s), −149.6 (d, J=20.8 Hz), −160.0 (br. s), −161.3 (t, J=16.1 Hz).

Example 22

1-Bis(pentafluorophenyl)boranyl-2-methyl(indenyl)
zirconium Trichloride, [1-$(C_6F_5)_2$B-(2-$CH_3$—$C_9H_5$)
$ZrCl_3$] (compound 22)

A solution of trimethylstannyl-2-methyl-bis (pentafluorophenyl)boranylindene (7.89 g, 12.2 mmol) in 30 ml of toluene was added at 0° C. to a suspension of zirconium tetrachloride, $ZrCl_4$, (2.84 g, 12.2 mmol) in 20 ml of toluene. The mixture was allowed to warm up to room temperature and stirred overnight under an argon atmosphere. The resulting orange-colored turbid solution was filtered to separate off minor insoluble components and the filtrate was evaporated to dryness. The orange-colored solid was taken up in 30 ml of hexane, stirred for 30 minutes and then filtered through a cannula. The solid was then washed again with hexane (2×20 ml) and dried under vacuum to give 6.71 g (82%) of a loose orange-colored solid.
NMR:
$^1$H (400.13 MHz, $CD_2Cl_2$), δ 7.88 (d, J=8.2 Hz, 1H), 7.59 (m, 1H), 7.47 (m, 2H), 7.29 (s, 1H), 2.42 (s, 3H).
$^{11}$B (128.4 MHz, $CD_2Cl_2$), δ 56.5 ppm (broad over a range of 45–65 ppm).
$^{19}$F (376.3 MHz, $CD_2Cl_2$), δ −128.9 (d, J=18.4 Hz, 4F, o-F), −149.2 (t, J=20 Hz, 2F, p-F), −160.6 (m, 4F, m-F).

Example 23

[Bis(pentafluorophenyl)boranyl-2-methyl-4-phenylindenyl]zirconium Trichloride, [1-$(F_5C_6)_2$B-2-$CH_3$-4-$C_6H_5$—$(C_9H_4)ZrCl_3$] (compound 23)

A solution of the crude product [bis(pentafluorophenyl) boranyl-2-methyltrimethylstannyl-4-phenylindene], 1-$(F_5C_6)$B-2-Me-3-$Me_3$Sn-4-Ph-$(C_9H_4)$, (8.72 g) in 35 ml of toluene was added at room temperature over 10 min to a suspension of zirconium tetrachloride, $ZrCl_4$, (2.85 g, 12.2 mmol) in 25 ml of toluene. The mixture assumed a red color and was stirred for 16 hours under an argon atmosphere. The resulting orange-yellow suspension was filtered through a cannula and the solid residue was washed with toluene (2×20 ml). The filtrate was combined with the washing solution and volatile components were removed under reduced pressure to leave a sticky orange solid, which was washed with dry hexane (2×15 ml) and filtered off. It was dried under vacuum to leave 2.0 g of an orange-colored powder containing the acceptor half-sandwich compound as crude product.

Example 24

Dimethylphosphinocyclopentadienylbis
(pentafluorophenyl)boranylcy
Clopentadienylzirconium Dichloride,
[$(C_5H_4)(CH_3)_2$PB$(C_6F_5)_2(C_5H_4)ZrCl_2$]
(compound 24)

A solution of trimethyldimethylphosphinocyclopentadiene, $Me_3$Si$(C_5H_4)$P$Me_2$, (0.315 g, 1.59 mmol) in 10 ml of toluene was added at room temperature over 5 min to a suspension of bis(pentafluorophenyl) boranylcyclopentadienylzirconium trichloride, [$(C_6F_5)_2$B$(C_5H_4)ZrCl_3$], (0.963 g, 1.59 mmol) in 10 ml of toluene. The mixture was heated for 15 hours in an oil bath at 80° C. The reaction mixture was cooled to room temperature and filtered over Célite to separate off minor insoluble components. The volatile components were stripped from the almost colorless filtrate to leave a dense, crystalline off-white solid, which had a purity of 90%, based on the title compound, according to $^1$H NMR. The product was washed with hexane (2×15 ml), dried under vacuum, resuspended in 15 ml of toluene and filtered over Célite to give a slightly yellowish solution. The solution was cooled to −35° C.; after standing for a number of days in the cold, crystals slowly begin to grow. 0.76 g of a crystalline solid was obtained (68.6%).
NMR:
$^1$H (400.13 MHz, $CD_2Cl_2$), δ 6.85 (m, 4H), 6.73 (m, 2H), 6.33 (s, 2H), 1.91 (d, J=10.6 Hz, 6H).
$^{11}$B (128.4 MHz, $CD_2Cl_2$), δ −11.9 (broad d, J=65 Hz).
$^{13}$C (100.58 MHz, $CD_2Cl_2$), δ 148.0 (dm, J=250 Hz), 140.5 (dm, J=244.6 Hz), 137.9 (dm, J=258.7 Hz), 124.6 (d, J=7 Hz), 123.3, 122.2, 118.5 (d, J=8 Hz), 110.4 (d, J=65.0 Hz), 14.2 (d, J=36.2 Hz).
$^{19}$F (376.3 MHz, $CD_2Cl_2$), δ −128.2 (d, J=23 Hz, 4F, o-F), −156.9 (t, J=21 Hz, 2F, p-F), −163.1 (m, 4F, m-F).
$^{31}$P (161.9 MHz, $CD_2Cl_2$), δ 2.7 (m),

Example 25

Diethylphosphinocyclopentadienylbis
(pentafluorophenyl)boranylcycl
Opentadienylzirconium Dichloride,
[$(C_5H_4)(C_2H_5)_2$PB$(C_6F_5)_2(C_5H_4)ZrCl_2$]
(compound 25)

A solution of trimethylsilyldiethylphosphinocyclopentadiene, $Me_3$Si$(C_5H_4)$P$Et_2$, (1.50 g, 6.63 mmol) in 20 ml of toluene was added at room temperature over 25 min through a cannula to a suspension of bis(pentafluorophenyl) boranylcyclopentadienylzirconium trichloride, [$(C_6F_5)_2$B$(C_5H_4)ZrCl_3$], (4.18 g, 6.89 mmol) in 60 ml of toluene. The mixture was heated for 24 hours in an oil bath at 100° C. The resulting slightly turbid solution was cooled to room temperature and filtered over Célite. The crystalline off-white solid which remained after volatile components had been stripped from the clear colorless filtrate under reduced pressure was washed with hexane (2×20 ml) and dried under vacuum to give 3.77 g (78.5%) of a white solid. The product, which was substantially pure according to NMR, was redissolved in the minimum volume of toluene, hexane was added to the clear solution up to the onset of turbidity and the mixture was cooled for a few weeks at −35° C. A micro-crystalline powder slowly deposited on the container wall. The supernatant was decanted and the product was dried under vacuum. It was pure according to NMR spectroscopy.
NMR:
$^1$H (400.13 MHz, $CD_2Cl_2$), δ 6.84 (4H), 6.76 (2H), 6.29 (2H), 2.56 (m, 2H), 2.18 (m, 2H), 1.06 (m, 6H).
$^{11}$B (128.4 MHz, $CD_2Cl_2$), δ −11.9 (d, J=67 Hz).
$^{19}$F (376.3 MHz, $CD_2Cl_2$), δ −127.8 (d, J=20 Hz, 4F, o-F), −157.1 (t, J=19 Hz, 2F, p-F), −163.2 (m, 4F, m-F).
$^{31}$P (161.9 MHz, $CD_2Cl_2$), δ 14.3 (m).

Example 26

Diisopropylphosphinocyclopentadienylbis
(pentafluorophenyl)borany
Icyclopentadienylzirconium Dichloride, [$(C_5H_4)$\{$(CH_3)_2$CH\}$_2$PB$(C_6F_5)_2(C_5H_4)ZrCl_2$]
(compound 26)

A solution of trimethylsilyldiisopropylphosphinocyclopentadiene, $Me_3$Si$(C_5H_4)$P$(CHMe_2)_2$, (1.59 g, 6.25 mmol) in 20 ml of toluene was added at room temperature over 20 min through a cannula to a suspension of bis(pentafluorophenyl)boranylcyclopentadienylzirconium trichloride, $(C_6F_5)_2B(C_5H_4)ZrCl_3$, (3.80 g, 6.26 mmol) in 50 ml of toluene. The resulting clear orange-red solution was heated for 24 hours in an oil bath at 100° C. to give a slightly turbid, light yellow solution. The reaction mixture was cooled to room temperature and filtered over Célite to separate off minor insoluble components. The volatile components were stripped from the filtrate under reduced pressure to leave a crystalline off-white solid. This was washed with dry hexane (2×10 ml) and dried under vacuum to give 4.01 g of a white powder (85%). The product was redissolved in the minimum volume of toluene and left to stand for two days at room temperature, during which time crystals began to grow. The solution was then stored for two weeks in a refrigerator at 4° C., after which the crystals were filtered off; they were suitable for X-ray structural analysis. The unit cell contains four molecules in different conformations, all of which are PB-bridged. d(PB)= 2.05–2.11 Angström.

Example 27

Diphenylphosphinocyclopentadienylbis(pentafluorophenyl)boranylcy Clopentadienylzirconium Dichloride, $[(C_5H_4)(C_6H_5)_2PB(C_6F_5)_2(C_5H_4)ZrCl_2]$ (compound 27)

A solution of trimethylsilyldiphenylphosphinocyclopentadiene (1.16 g, 3.61 mmol) in 13 ml of toluene was added at room temperature to a suspension of bis(pentafluorophenyl)boranylcyclopentadienylzirconium trichloride (2.25 g, 3.71 mmol) in 25 ml of toluene. The mixture was heated for 24 hours in an oil bath at 110° C. The slightly turbid reaction solution was cooled to room temperature and filtered over Célite to separate off minor insoluble components. The volatile components were stripped from the clear filtrate under reduced pressure to leave a powdery off-white solid, which was washed with hexane (2×15 ml) and then with toluene (15 ml) and dried under vacuum to give 2.53 g of a white powder (85%). The product is pure according to NMR.
NMR:
$^1$H (400.13 MHz, $CD_2Cl_2$), δ: broad resonances between 7.6 and 6.2 ppm, indicating dynamic processes in solution.
$^{11}$B (128.4 MHz, $CD_2Cl_2$), δ –7.9.
$^{31}$P (161.9 MHz, $CD_2Cl_2$), δ 22.4.

Example 28

1-Dimethylphosphino-2-methylindenylbis(pentafluorophenyl)boranylcyclopentadienylzirconium Dichloride, $[(2-CH_3—C_9H_5)(CH_3)_2PB(C_6F_5)_2(C_5H_4)ZrCl_2]$ (compound 28)

A solution of 1-trimethylstannyl-2-methyl-3-dimethylphosphinoindene, $1-Me_3Sn-2-Me-3-Me_2P(C_9H_5)$, (1.18 g, 3.34 mmol) in 23 ml of toluene was added at 0° C. over 15 minutes to a suspension of bis(pentafluorophenyl)boranylcyclopentadienylzirconium trichloride, $(C_6F_5)_2BCpZrCl_3$, (2.08 g, 3.43 mmol) in 30 ml of toluene. The resulting turbid yellow mixture was stirred for 16 hours at room temperature under argon. The slightly turbid solution was filtered over Célite and volatile components were removed under reduced pressure to leave a yellow solid, which was taken up in 20 ml of hexane and stirred for 20 minutes. The fine suspension was filtered and the solid was washed a further twice with hexane (2×20 ml). It was dried under vacuum to give 2.40 g of substance (94%).
NMR:
$^1$H (400.13 MHz, $CD_2Cl_2$), δ 7.74 (d, J=8.52 Hz, 1H), 7.68 (d, J=8.94 Hz, 1H), 7.46 (m, 1H), 6.82 (d, J=2.45 Hz, 1H), 6.62 (m, 1H), 6.52 (m, 1H), 6.31 (s, 1H), 5.98 (s, 1H), 2.51 (s, 3H), 2.13 (d, J=10.75 Hz, 3H), 2.03 (d, J=10.55 Hz, 3H).
$^{11}$B (128.4 MHz, $CD_2Cl_2$), δ –9.68 ppm (d, J=56.8 Hz).
$^{19}$F (376.3 MHz, $CD_2Cl_2$), δ –126.2 (s, 2F), –126.6 (s, 2F), –157.1 (m, 2F), –162.9 (m, 4F).
$^{31}$P (161.9 MHz, $CD_2Cl_2$), δ 10.48 ppm.

Example 29

1-Diethylphosphino-2-methylindenylbis(pentafluorophenyl)boranylcyclopentadienylzirconium Dichloride, $[2-CH_3—C_9H_5(C_2H_5)_2PB(C_6F_5)_2(C_2H_4)ZrCl_2]$ (compound 29)

A solution of 1-trimethylstannyl-2-methyl-3-diethylphosphinoindene, $1-Me_3Sn-2-Me3-Et_2P-(C_9H_5)$, (0.476 g, 1.25 mmol) in 15 ml of toluene was added at room temperature over 10 minutes to a suspension of bis(pentafluorophenyl)boranylcyclopentadienylzirconium trichloride, $(C_6F_5)_2B(C_5H_4)ZrCl_3$, (0.758 g, 1.25 mmol) in 15 ml of toluene. The turbid solution was stirred for 18 hours, after which the slightly turbid solution was filtered over Célite to separate off minor insoluble components. The filtrate was evaporated to dryness under reduced pressure. The yellow solid was taken up in 20 ml of hexane and stirred for 30 minutes. The suspension was filtered and the solid was washed with pentane (2×10 ml) and dried under vacuum to yield 0.837 g (85%) of a powdery yellow product. The product is pure according to NMR spectroscopy.
NMR:
$^1$H (400.13 MHz, $C_6D_6$), δ 7.45 (d, J=7.72 Hz, 1H), 7.28 (d, J=8.41 Hz, 1H), 7.06 (t, J=7.18 Hz, 1H), 6.72 (t, J=8.14 Hz, 1H), 6.46 (m, 1H), 6.35 (m, 2H), 6.12 (s, 1H), 5.75 (s, 1H), 2.20 (m, 1H), 2.07 (s, 3H), 2.02 (m, 1H), 1.78 (m, 2H), 0.26 (m, 6H).
$^{11}$B (128.4 MHz, $C_6D_6$), δ –9.1 ppm.
$^{19}$F (376.3 MHz, $C_6D_6$), δ –124.9 (d, J=13.5 Hz, 2F, o-F), –125.2 (d, J=13.2 Hz, 2F, o-F), –155.4 (t, J=21.8 Hz, 1F, p-F), –155.7 (t, J=21.0 Hz, 1F, p-F), –162.1 (m, 4F, m-F).
$^{31}$P (161.9 MHz, $C_6D_6$), δ 28.1 ppm.

Example 30

1-Dimethylphosphino-2-methylindenyl-1'-bis(pentafluorophenyl)boranyl-2'-methylindenylzirconium Dichloride, $[(2-CH_3—C_9H_5)—(CH_3)_2PB(C_6F_5)_2-(2-CH_3—C_9H_5)ZrCl_2]$ (compound 30)

A solution of 1-trimethylstannyl-2-methyl-3-dimethylphosphinoindene, $1-Me_3Sn-2Me-3-Me_2P-C_9H_5$, (0.598 g, 1.69 mmol) in 18 ml of toluene was added at room temperature over 10 minutes through a cannula to a suspension of 1-bis(pentafluorophenyl)boranyl-2-methylindenylzirconium trichloride, $[1-(C_6F_5)_2B-2-Me(C_9H_5)ZrCl_3]$, (1.136 g, 1.69 mmol) in 30 ml of toluene. The slightly turbid solution was heated for 6 hours in an oil bath at 60° C., with stirring, during which time a large amount of a yellow solid formed. The reaction mixture was cooled to room temperature and the supernatant was filtered through a cannula into another Schlenk tube. The solid was washed with toluene (3×5 ml) and hexane (2×5 ml), after which the washing solutions were combined with the filtrate. The remaining solid was dried under vacuum to give 0.71 g (50.8%) of a light yellow microcrystalline solid. The NMR spectra of this solid in $CD_2Cl_2$ show mainly the rac isomer (rac isomer:meso isomer=90:10). The filtrate combined with the washing solutions was evaporated to dryness and the residue was washed with hexane (2×20 ml) and dried under vacuum to give 0.67 g (48%) of a powdery yellow product. The NMR spectra in $CD_2Cl_2$ show mainly the meso isomer (rac isomer:meso isomer=20:80). The total yield of the reaction is more than 98% and the ratio of rac to meso is 62:38 under these reaction conditions.

NMR:

$^1H$ (400.13 MHz, $CD_2Cl_2$):

rac isomer δ 7.71 (d, J=8.7 Hz, 1H), 7.55 (m, 2H), 7.38 (m, 2H), 7.26 (d, J=7.6 Hz, 1H), 7.05 (m, 1H), 6.73 (s, 1H), 6.65 (d, J=2.1 Hz, 1H), 2.26 (d, broadened, J=10.7 Hz, 6H), 2.24 (s, 3H), 1.70 (s, 3H).

meso isomer δ 7.71 (d, J=8.6 Hz, 1H), 7.47 (d, J=8.5 Hz, 1H), 7.40 (d, J=8.5 Hz, 1H), 7.26 (t, J=6.7 Hz, 1H), 7.04 (t, J=8.0 Hz, 2H), 6.79 (s, 1H), 6.60 (s, 1H), 6.56 (s, 2H), 2.59 (s, 3H), 2.43 (s, 3H), 2.27 (dd, J=9.8 Hz, 6H).

$^{11}B$ (128.4 MHz, $CD_2Cl_2$):

rac isomer δ −7.09 (singlet).

meso isomer δ −7.04 (singlet).

$^{19}F$ (376.3 MHz, $CD_2Cl_2$):

rac isomer δ −124.6 (m, 1F, o-F), −127.2 (broad s, 2F, o-F), −128.6 (m, 1F, o-F), −157.3 (t, J=20.8 Hz, 1F, p-F), −157.6 (t, J=20.5 Hz, 1F, p-F), −161.8 (m, 1F, m-F), −163.0 (m, 2F, m-F), −163.7 (m, 1F, m-F).

meso isomer δ −124.2 (m, 1F, o-F), −127.6 (broad, 3F, o-F), −157.4 (m, 2F, p-F), −161 to −163 (broad, 4F, m-F).

$^{31}P$ (161.9 MHz, $CD_2Cl_2$):

rac isomer δ 18.9 (broad multiplet).

meso isomer δ 17.75 (broad multiplet).

Example 31

9-Diethylphosphinofluorenylbis(pentafluorophenyl) boranylcyclopentadienylzirconium Dichloride, [$(C_{13}H_8)(C_2H_5)_2PB(C_6F_5)_2(C_5H_4)ZrCl_2$] (compound 31)

A solution of bis(pentafluorophenyl) boranylcyclopentadienylzirconium trichloride, $(F_5C_6)_2$ $BCpZrCl_3$, (0.548 g, 0.903 mmol) in 25 ml of toluene was added at room temperature over 10 min through a cannula to a suspension of 9-diethylphosphinofluorenyllithium, Li[9-$Et_2P$-$(C_{13}H_8)$], (0.235 g, 0.903 mmol) in 15 ml of toluene. The mixture became brownish-red after the addition had ended. After stirring overnight under an Ar atmosphere, the turbid solution was filtered over Célite to separate off LiCl. The clear orange-red solution was evaporated to dryness to leave a dense orange-colored solid, which was washed with pentane (2×15 ml) and dried to give 0.71 g (95%) of a dense, microcrystalline yellowish-orange solid. This was the title compound according to NMR analysis.

Characterization by NMR spectroscopy:

$^1H$ (400.13 MHz, $C_6D_6$), δ 7.94 (d, J=8.3 Hz, 2H), 7.53 (d, J=8.6 Hz, 2H), 7.45 (pseudo-t, J=7.7 Hz, 2H), 7.19 (pseudo-t, J=8.3 Hz, 2H), 6.37 (m, 2H), 6.06 (s, 2H), 2.42 (m, 2H), 2.04 (m, 2H), 0.38 (m, 6H).

$^{11}B$ (128.4 MHz, $C_6D_6$), δ −9.3 (br. s).

$^{19}F$ (376.9 MHz, $C_6D_6$), δ −125.2 (d, J=22 Hz, 4F, o-F), −155.5 (t, J=21 Hz, 2F, p-F), −162.2 (t, J=22 Hz, 4F, m-F).

31P (161.9 MHz, $C_6D_6$), δ 35.1 (br. s).

Example 32

9-Diethylphosphinofluorenyl-1-bis (pentafluorophenyl)boranyl-2-methylindenylzirconium Dichloride, [$(C_{13}H_8)$—$(C_2H_5)_2PB(C_6F_5)_2$-$(2-CH_3$—$C_9H_5)ZrCl_2$] (compound 32)

A solution of 1-bis(pentafluorophenyl)boranyl-2-methylindenylzirconium trichloride, [1-$(F_5C_6)_2B$-2-Me-$(C_9H_5)ZrCl_3$], (0.75 g, 1.11 mmol) in 30 ml of toluene was added at room temperature over 10 min through a cannula to a suspension of 9-diethylphosphino-fluorenyllithium, Li[9-$Et_2P$-$(C_{13}H_8)$], (0.29 g, 1.11 mmol) in 15 ml of toluene. The orange-red suspension was stirred overnight under an Ar atmosphere and then filtered over Célite, after which the solid was washed with $CH_2Cl_2$ to improve the dissolution of the product. The orange-colored residue remaining after evaporation of the combined filtrates to dryness was washed with pentane (3×15 ml). The orange-colored powder was dried under high vacuum (1.0×10$^{-3}$ mbar) to leave 0.81 g (82%) of product in the form of an orange-colored powder. This was the title compound, [$(C_{13}H_8)$-9-$Et_2PB(C_6F_5)_2$-2-Me-$(C_9H_5)ZrCl_2$], according to NMR spectroscopic analysis.

Characterization by NMR spectroscopy:

$^1H$ (400.13 MHz, $C_6D_6$), δ 7.75 (t, J=8.7 Hz, 2H), 7.66 (d, J=8.2 Hz, 1H), 7.50 (t, J=8.5 Hz, 2H), 7.43 (d, J=8.9 Hz, 1H), 7.34 (d, J=8.4 Hz, 1H), 7.29 (d, J=8.4 Hz, 1H), 7.17 (t, J=8.3 Hz, 1H), 6.99 (t, J=8.3 Hz, 1H), 6.97 (t, J=8.1 Hz, 1H), 6.76 (t, J=7.8 Hz, 1H), 6.60 (s, 1H), 2.93–2.87 (m, 1H), 2.63–2.43 (m, 3H), 0.65 (m, J=7.3 Hz, 3H), 0.52 (m, 3H).

$^{11}B$ (128.4 MHz, $C_6D_6$), δ −6.20 ppm (broad singlet).

$^{19}F$ (376.3 MHz, $C_6D_6$), δ −126.3 (s, 3F, o-F), −130.1 (m, 1F, o-F), −155.7 (m, 2F, p-F), −160.5 (m, 1F, m-F), −162.2 (s, 3F, m-F).

$^{31}P$ (161.9 MHz, $C_6D_6$), δ 45.3 ppm (br. s).

Example 33

1-Diethylphosphino-2-methyl-4-phenyl(indenyl)-1-bis(pentafluorophenyl)boranyl-2-methyl-4-phenyl (indenyl)zirconium Dichloride, [$(2-CH_3$-4-$C_6H_5$—$C_9H_4)$—$(C_2H_5)_2PB(C_6F_5)_2$-$(2-CH_3$-4-$C_6H_5$—$C_9H_4)$$ZrCl_2$] (compound 33)

A solution of 1-diethylphosphino-2-methyl-3-trimethylstannyl-4-phenylindene, (1$Et_2P$-2-Me-3-$Me_3Sn$-4-Ph-$C_9H_4$), (0.404 g, 0.877 mmol) in 10 ml of toluene was added dropwise at room temperature over 10 min to a solution of the acceptor half-sandwich crude product bis (pentafluorophenyl)boranyl-2-methyl-4-phenylindenylzirconium trichloride, [$(F_5C_6)_2B$-2-Me-4-Ph-$(C_9H_4)ZrCl_3$], (0.655 g) in 10 ml of toluene. The mixture immediately became turbid and a large amount of an orange-colored precipitate formed after the addition had ended. The mixture was stirred for 16 hours at room temperature. The suspension was then filtered and the solid was washed with toluene (2×6 ml). The filtrate combined with the washing solutions was evaporated to dryness to give a solid, which was taken up in 15 ml of dry hexane, stirred for 15 min and filtered off. The orange-colored solid was then washed again with hexane (2×6 ml) and filtered off. The solid residue was dried under high vacuum to give 0.46 g of an orange-colored powder. This crude product, corresponding to the title compound, was used for polymerization without Purification.

Example 34

Ethylene Polymerization 100 ml of dry toluene distilled under inert gas were placed in a dry, oxygen-free 300 ml V4A steel autoclave and the catalyst was added at 60° C. by means of a syringe. The catalyst used was 5×10$^{-8}$ mol of [(cp)$Et_2PB(C_6F_5)_2$(cp) $ZrCl_2$] (compound no. 25) in 0.33 ml of a 10% toluene solution of MAO (0.5 mmol). The pressure was kept constant at 10 bar with ethylene. The polymerization took place over the temperature range 60° to 72° C. and was stopped after 30 minutes. The polyethylene formed was extracted by stirring with 90/10 ethanol/hydrochloric acid, filtered off, washed with ethanol and dried to constant weight in a vacuum drying cabinet at 80° C.

| | |
|---|---|
| Polymer yield: | 3.7 g |
| Catalyst activity: | 148 tons of PE per mol of Zr per hour |

Intrinsic viscosity in ortho-dichlorobenzene at 140° C.: [η]=3.56 dl/g

| | | |
|---|---|---|
| GC (universal calibration using polystyrene standards): | | $M_w$ = 356 kg/mol $M_n$ = 141 kg/mol |
| DSC (2nd heating): | melting temperature: | $T_m$ = 139° C. |
| | enthalpy of fusion: | $H_m$ = 176 J/g |

Example 35

Ethylene Polymerization 100 ml of dry toluene distilled under inert gas were placed in a dry, oxygen-free 300 ml V4A steel autoclave and the catalyst was added at 80° C. by means of a syringe. The catalyst used was $1\times10^{-7}$ mol of [(flu)Et$_2$PB(C$_6$F$_5$)$_2$(cp)ZrCl$_2$] (compound no. 31) in 0.66 ml of a 10% toluene solution of MAO (1 mmol). The pressure was kept constant at 10 bar with ethylene. The polymerization took place over the temperature range 80° to 88° C. and was stopped after 30 minutes. The polyethylene formed was extracted by stirring with 90/10 ethanol/hydrochloric acid, filtered off, washed with ethanol and dried to constant weight in a vacuum drying cabinet at 80° C.

| | |
|---|---|
| Polymer yield: | 2.9 g |
| Catalyst activity: | 58 tons of PE per mol of Zr per hour |

Intrinsic viscosity in ortho-dichlorobenzene at 140° C.: [η]=7.86 dl/g

| | |
|---|---|
| GC (universal calibration using polystyrene standards): | $M_w$ = 1306 kg/mol $M_n$ = 102 kg/mol |

High temperature GC coupled with viscometry: The polymer is long-chain branched.

| | | |
|---|---|---|
| DSC (2nd heating): | melting temperature: | $T_m$ = 139° C. |
| | enthalpy of fusion: | $H_m$ = 166 J/g |

Example 36

Ethylene Polymerization 100 ml of dry toluene distilled under inert gas were placed in a dry, oxygen-free 300 ml V4A steel autoclave and the catalyst was added at 60° C. by means of a syringe. The catalyst used was $1\times10^{-7}$ mol of [(flu)Et$_2$PB(C$_6$F$_5$)$_2$(cp)ZrCl$_2$] (compound no. 31) in 0.66 ml of a 10% toluene solution of MAO (1 mmol). The pressure was kept constant at 10 bar with ethylene. The polymerization took place over the temperature range 60°-66° C. and was stopped after 30 minutes. The polyethylene formed was extracted by stirring with 90/10 ethanol/hydrochloric acid, filtered off, washed with ethanol and dried to constant weight in a vacuum drying cabinet at 80° C.

| | |
|---|---|
| Polymer yield: | 2.6 g |
| Catalyst activity: | 52 tons of PE per mol of Zr per hour |

Intrinsic viscosity in ortho-dichlorobenzene at 140° C.: [η]=13.25 dl/g

| | |
|---|---|
| GC (universal calibration using polystyrene standards): | $M_w$ = 11,120 kg/mol $M_n$ = 1420 kg/mol |

High temperature GC coupled with viscometry: The polymer is long-chain branched.

| | | |
|---|---|---|
| DSC (2nd heating): | melting temperature: | $T_m$ = 137° C. |
| | enthalpy of fusion: | $H_m$ = 139 J/g |

Example 37

Propylene Polymerization

Approx. 1 mol of propylene was placed in a dry, oxygen-free 300 ml V4A steel autoclave and bulk polymerization was started at 20° C. by adding the catalyst by means of a pressure lock. The catalyst used was $1\times10^{-6}$ mol of [(2-Me-ind)Me$_2$PB(C$_6$F$_5$)$_2$(cp)ZrCl$_2$] (compound no. 28) in 6.6 ml of a 10% toluene solution of MAO (10 mmol). The polymerization took place over the temperature range 20°–25° C. and was stopped after 30 minutes. The polypropylene formed was extracted by stirring with 90/10 ethanol/hydrochloric acid, filtered off, washed with ethanol and dried to constant weight in a vacuum drying cabinet at 80° C.

| | |
|---|---|
| Polymer yield: | 14.4 g |
| Catalyst activity: | 28.8 tons of PP per mol of Zr per hour |
| NMR (triad analysis): | 37% isotactic |
| | 41% atactic |
| | 22% syndiotactic |

Intrinsic viscosity in ortho-dichlorobenzene at 140° C.: [η]1.13 dl/g

| | | |
|---|---|---|
| GC (universal calibration using polystyrene standards): | | $M_w$ = 157 kg/mol $M_n$ = 88 kg/mol |
| DSC (2nd heating): | amorphous PP | $T_g$ = −4° C. |

Example 38

Propylene Polymerization

Approx. 1 mol of propylene was placed in a dry, oxygen-free 300 ml V4A steel autoclave and bulk polymerization was started at 20° C. by adding the catalyst by means of a pressure lock. The catalyst used was 1×10$^{-6}$ mol of rac-[(2-Me-ind)Me$_2$PB(C$_6$F$_5$)$_2$(2-Me-ind)ZrCl$_2$] (compound no. 30-rac) in 1 ml of a 1 molar toluene solution of TIBA (100 μmol) and 4 μmol of N,N-dimethylanilinium tetrakispentafluorophenylborate in toluene (1 μmol/1 ml). The polymerization took place over the temperature range 20°–25° C. and was stopped after 30 minutes. The polypropylene formed was extracted by stirring with 90/10 ethanol/hydrochloric acid, filtered off, washed with ethanol and dried to constant weight in a vacuum drying cabinet at 80° C.

| Polymer yield: | 4.6 g |
|---|---|
| Catalyst activity: | 9.2 tons of PP per mol of Zr per hour |
| NMR (triad analysis): | 93% isotactic |
| | 5% atactic |
| | 2% syndiotactic |

Intrinsic viscosity in ortho-dichlorobenzene at 140° C.: [η]=4.38 dl/g

| GC (universal calibration using polystyrene standards): | | M$_w$ = 1289 kg/mol |
|---|---|---|
| | | M$_n$ = 313 kg/mol |
| DSC (1st heating): | melting temperature: | T$_m$ =156° C. |
| | enthalpy of fusion: | H$_m$ = 115 J/g |
| (2nd heating): | melting temperature: | T$_m$ = 151° C. |
| | enthalpy of fusion: | H$_m$ = 101 J/g |

Example 39

Propylene Polymerization

Approx. 1 mol of propylene was placed in a dry, oxygen-free 300 ml V4A steel autoclave and bulk polymerization was started at approx. 55° C. by adding the catalyst by means of a pressure lock. The catalyst used was 0.974 mg of crude rac-[(2-Me-4-Ph-ind)Et$_2$PB(C$_6$F$_5$)$_2$(2-Me-4-Ph-ind)ZrCl$_2$] (from Example 33) in 6.6 ml of a 10% toluene solution of MAO (10 mmol). The polymerization took place over the temperature range 55°–60° C. and was stopped after 30 minutes. The polypropylene formed was extracted by stirring with 90/10 ethanol/hydrochloric acid, filtered off, washed with ethanol and dried to constant weight in a vacuum drying cabinet at 80° C.

| Polymer yield: | 20.3 g |
|---|---|
| NMR (triad analysis): | 99% isotactic |
| | 1% atactic |
| | 0% syndiotactic |

Intrinsic viscosity in ortho-dichlorobenzene at 140° C.: [η]=2.01 dl/g

| DSC (2nd heating): | melting temperature: | T$_m$ = 161° C. |
|---|---|---|
| | enthalpy of fusion: | H$_m$ = 92 J/g |

If the polymerization was carried out analogously in the temperature range 68°–72° C., the measured intrinsic viscosity in ODCB (ortho-dichlorobenzene at 140° C.) was still 1.95 dl/g and the DSC measurement (2nd heating) gave a melting maximum T$_m$ of 161° C.

Example 40

Propylene Polymerization

Approx. 1 mol of propylene was placed in a dry, oxygen-free 300 ml V4A steel autoclave and bulk polymerization was started at 20° C. by adding the catalyst by means of a pressure lock. The catalyst used was 1×10$^{-6}$ mol of [(flu)Et$_2$PB(C$_6$F$_5$)$_2$(cp)ZrCl$_2$] (compound no. 31) in 6.6 ml of a 10% toluene solution of MAO (10 mmol). The polymerization took place over the temperature range 20°–24° C. and was stopped after 30 minutes. The polypropylene formed was extracted by stirring with 90/10 ethanol/hydrochloric acid, filtered off, washed with ethanol and dried to constant weight in a vacuum drying cabinet at 80° C.

| Polymer yield: | 8.3 g |
|---|---|
| Catalyst activity: | 16.6 tons of PP per mol of Zr per hour |
| NMR (triad analysis): | 15% isotactic |
| | 41% atactic |
| | 45% syndiotactic |

Intrinsic viscosity in ortho-dichlorobenzene at 140° C.: [η]=2.78 dl/g

| GC (universal calibration using polystyrene standards): | M$_w$ = 534 kg/mol |
|---|---|
| | M$_n$ = 236 kg/mol |

High temperature GC coupled with viscometry: The polymer is long-chain branched.

| DSC (2nd heating): | amorphous PP | T$_g$ = −1° C. |
|---|---|---|

Example 41

Propylene Polymerization

Approx. 1 mol of propylene was placed in a dry, oxygen-free 300 ml V4A steel autoclave and bulk polymerization was started at 20° C. by adding the catalyst by means of a pressure lock. The catalyst used was 1×10$^{-6}$ mol of [(flu)Et$_2$PB(C$_6$F$_5$)$_2$(2-Me-ind)ZrCl$_2$] (compound no. 32) in 6.6 ml of a 10% toluene solution of MAO (10 mmol). The polymerization took place over the temperature range 20°–23° C. and was stopped after 60 minutes. The polypropylene formed was extracted by stirring with 90/10 ethanol/hydrochloric acid, filtered off, washed with ethanol and dried to constant weight in a vacuum drying cabinet at 80° C.

| Polymer yield: | 14.5 g |
|---|---|
| Catalyst activity: | 14.5 tons of PP per mol of Zr per hour |
| NMR (triad analysis): | 68% isotactic |
| | 21% atactic |
| | 11% syndiotactic |

Intrinsic viscosity in ortho-dichlorobenzene at 140° C: $[\eta]$= 1.04 dl/g

| DSC (2nd heating): | glass transition temperature: | $T_g$ = −6° C. |
|---|---|---|
| | melting peak: | $T_m$ = 148° C. |
| | enthalpy of fusion: | $H_m$ = 32 J/g |

Example 42

Ethylene/Propylene Copolymerization 100 ml of dry toluene distilled under inert gas and 10 g of propylene were placed in a dry, oxygen-free 300 ml V4A steel autoclave. At an internal temperature of 40° C., the pressure was raised from 3 bar to 4 bar with ethylene. The catalyst used was $2.5\times10^{-7}$ mol of $[(cp)Me_2PB(C_6F_5)_2(cp)ZrCl_2]$ (compound no. 24) in 0.25 ml of a 1 molar toluene solution of TIBA (25 µmol) and 1 µmol of N,N-dimethylanilinium tetrakispentafluorophenylborate in chlorobenzene (1 µmol/1 ml). The catalyst was added by means of a pressure lock and the pressure was raised from 4 bar to 5 bar. The polymerization took place over the temperature range 40°–44° C. and was stopped after 30 minutes.

The polymer formed was extracted by stirring with 90/10 ethanol/hydrochloric acid, filtered off, washed with ethanol and dried to constant weight in a vacuum drying cabinet at 80° C.

| Polymer yield: | 3.5 g | |
|---|---|---|
| Catalyst activity: | 28.0 tons of EP rubber per mol of Zr per hour | |
| FTIR: | propylene: | 55 wt. % |
| | ethylene: | 45 wt. % |

Intrinsic viscosity in ortho-dichlorobenzene at 140° C.: $[\eta]$=2.12 dl/g

| GC (universal calibration using polystyrene standards): | $M_w$ = 139 kg/mol |
| | $M_n$ = 106 kg/mol |
| DSC: | amorphous copolymer $T_g$ = −57° C. |

Example 43

Ethylene/Propylene Copolymerization 100 ml of dry toluene distilled under inert gas and 10 g of propylene were placed in a dry, oxygen-free 300 ml V4A steel autoclave. At an internal temperature of 40° C., the pressure was raised from 3 bar to 4 bar with ethylene. The catalyst used was $2.5\times10^{-7}$ mol of $[(2\text{-Me-ind})Me_2PB(C_6F_5)_2(cp)ZrCl_2]$ (compound no. 28) in 1.65 ml of a 10% toluene solution of MAO (2.5 mmol). The catalyst was added by means of a pressure lock and the pressure was raised from 4 bar to 5 bar. The polymerization took place over the temperature range 40°–44° C. and was stopped after 30 minutes.

The polymer formed was extracted by stirring with 90/10 ethanol/hydrochloric acid, filtered off, washed with ethanol and dried to constant weight in a vacuum drying cabinet at 80° C.

| Polymer yield: | 5.2 g | |
|---|---|---|
| Catalyst activity: | 41.6 tons of EP rubber per mol of Zr per hour | |
| FTIR: | propylene: | 41 wt. % |
| | ethylene: | 59 wt. % |

Intrinsic viscosity in ortho-dichlorobenzene at 140° C.: $[\eta]$=2.29 dl/g

| GC (universal calibration using polystyrene standards): | $M_w$ = 243 kg/mol |
| | $M_n$ = 94 kg/mol |
| DSC (2nd heating): glass transition temperature: | $T_g$ = −57° C. |
| enthalpy of fusion: | $H_m$ = 23 J/g |

Example 44

Ethylene/Propylene Copolymerization 100 ml of dry toluene distilled under inert gas and 10 g of propylene were placed in a dry, oxygen-free 300 ml V4A steel autoclave. At an internal temperature of 20° C., the pressure was raised from 2 bar to 3 bar with ethylene. The catalyst used was $2.5\times10^{-7}$ mol of rac-$[(2\text{-Me-ind})Me_2PB(C_6F_5)_2(2\text{-Me-ind})ZrCl_2]$ (compound no. 30-rac) in 1.65 ml of a 10% toluene solution of MAO (2.5 mmol). The catalyst was added by means of a pressure lock and the pressure was raised from 3 bar to 4 bar. The polymerization took place over the temperature range 20°–23° C. and was stopped after 30 minutes.

The polymer formed was extracted by stirring with 90/10 ethanol/hydrochloric acid, filtered off, washed with ethanol and dried to constant weight in a vacuum drying cabinet at 80° C.

| Polymer yield: | 5.9 g | |
|---|---|---|
| Catalyst activity: | 47.2 tons of EP rubber per mol of Zr per hour | |
| FTIR: | propylene: | 63 wt. % |
| | ethylene: | 37 wt. % |

Intrinsic viscosity in ortho-dichlorobenzene at 140° C.: $[\eta]$=2.33 dl/g

| GC (universal calibration using polystyrene standards): | | $M_w$ = 272 kg/mol |
| | | $M_n$ = 125 kg/mol |
| DSC (2nd heating): | glass transition temperature: | $T_g$ = −59° C. |
| | enthalpy of fusion: | $H_m$ = 7 J/g |
| | melting peak: | $T_m$ = −29° C. |

Example 45

Ethylene/Propylene Copolymerization 100 ml of dry toluene distilled under inert gas and 10 g of propylene were placed in a dry, oxygen-free 300 ml V4A steel autoclave. At an internal temperature of 20° C., the pressure was raised from 2 bar to 3 bar with ethylene. The catalyst used was $5\times10^{-7}$ mol of $[(\text{flu})Et_2PB(C_6F_5)_2(cp)ZrCl_2]$ (compound no. 31) in 3.3 ml of a 10% toluene solution of MAO (5 mmol). The catalyst was added by means of a pressure lock and the pressure was raised from 3 bar to 4 bar. The polymerization took place over the temperature range 20°–24° C. and was stopped after 30 minutes.

The polymer formed was extracted by stirring with 90/10 ethanol/hydrochloric acid, filtered off, washed with ethanol and dried to constant weight in a vacuum drying cabinet at 80° C.

| Polymer yield: | 8.0 g | |
|---|---|---|
| Catalyst activity: | 32.0 tons of EP rubber per mol of Zr per hour | |
| FTIR: | propylene: | 89 wt. % |
| | ethylene: | 11 wt. % |

Intrinsic viscosity in ortho-dichlorobenzene at 140° C.: [η]=2.76 dl/g

| GC (universal calibration using polystyrene standards): | $M_w$ = 467 kg/mol |
|---|---|
| | $M_n$ = 104 kg/mol |

High temperature GC coupled with viscometry: The polymer is long-chain branched.

| DSC: | amorphous copolymer | $T_g$ = −36° C./−16° C. |
|---|---|---|

Example 46

Ethylene/Propylene Copolymerization 100 ml of dry toluene distilled under inert gas and 10 g of propylene were placed in a dry, oxygen-free 300 ml V4A steel autoclave. At an internal temperature of 40° C., the pressure was raised from 3 bar to 4 bar with ethylene. The catalyst used was $2.5 \times 10^{-7}$ mol of [(flu)Et$_2$PB(C$_6$F$_5$)$_2$(cp)ZrCl$_2$] (compound no. 31) in 1.65 ml of a 10% toluene solution of MAO (2.5 mmol). The catalyst was added by means of a pressure lock and the pressure was raised from 4 bar to 5 bar. The polymerization took place over the temperature range 40°–44° C. and was stopped after 30 minutes.

The polymer formed was extracted by stirring with 90/10 ethanol/hydrochloric acid, filtered off, washed with ethanol and dried to constant weight in a vacuum drying cabinet at 80° C.

| Polymer yield: | 5.6 g | |
|---|---|---|
| Catalyst activity: | 44.8 ton of EP rubber per mol of Zr per hour | |
| FTIR: | propylene: | 79 wt. % |
| | ethylene: | 21 wt. % |

Intrinsic viscosity in ortho-dichlorobenzene at 140° C.: [η]=3.02 dl/g

| GC (universal calibration using polystyrene standards): | $M_w$ = 422 kg/mol |
|---|---|
| | $M_n$ = 173 kg/mol |

High temperature GC coupled with viscometry: The polymer is long-chain branched.

| DSC: | amorphous copolymer | $T_g$ = −38° C./−24° C. |
|---|---|---|

Example 47

Ethylene/Propylene Copolymerization 100 ml of dry toluene distilled under inert gas and 10 g of propylene were placed in a dry, oxygen-free 300 ml V4A steel autoclave. At an internal temperature of 40° C., the pressure was raised from 3 bar to 5 bar with ethylene. The catalyst used was $2.5 \times 10^{-7}$ mol [(flu)Et$_2$PB(C$_6$F$_5$)$_2$(cp)ZrCl$_2$] (compound no. 31) in 1.65 ml of a 10% toluene solution of MAO (2.5 mmol). The catalyst was added by means of a pressure lock and the pressure was raised from 5 bar to 7 bar. The polymerization took place over the temperature range 40°–48° C. and was stopped after 30 minutes.

The polymer formed was extracted by stirring with 90/10 ethanol/hydrochloric acid, filtered off, washed with ethanol and dried to constant weight in a vacuum drying cabinet at 80° C.

| Polymer yield: | 5.7 g | |
|---|---|---|
| Catalyst activity: | 45.6 tons of EP rubber per mol of Zr per hour | |
| FTIR: | propylene: | 65 wt. % |
| | ethylene: | 35 wt. % |

Intrinsic viscosity in ortho-dichlorobenzene at 140° C.: [η]=4.35 dl/g

| GC (universal calibration using polystyrene standards): | $M_w$ = 659 kg/mol |
|---|---|
| | $M_n$ = 248 kg/mol |

High temperature GC coupled with viscometry: The polymer is long-chain branched.

| DSC: | amorphous copolymer | $T_g$ = −51° C. |
|---|---|---|

Example 48

Ethylene/Propylene/Ethylidenenorbornene Terpolymerization 100 ml of dry toluene distilled under inert gas, 10 g of propylene and 2 g of 5-ethylidene-2-norbornene were placed in a dry, oxygen-free 300 ml V4A steel autoclave. At an internal temperature of 80° C., the pressure was raised from 5.5 bar to 7.5 bar with ethylene. The catalyst used was $2.5 \times 10^{-7}$ mol of [(flu)Et$_2$PB(C$_6$F$_5$)$_2$(cp)ZrCl$_2$] (compound no. 31) in 1.65 ml of a 10% toluene solution of MAO (2.5 mmol). The catalyst was added by means of a pressure lock and the pressure was raised from 7.5 bar to 9.5 bar. The polymerization took place over the temperature range 80°–82° C. and was stopped after 30 minutes. The polymer formed was extracted by stirring with 90/10 ethanol/ hydrochloric acid, filtered off, washed with ethanol and dried to constant weight in a vacuum drying cabinet at 80° C.

| | |
|---|---|
| Polymer yield: | 5.4 g |
| Catalyst activity: | 43.2 tons of EP rubber per mol of Zr per hour |
| FTIR: | propylene: 34 wt. % |
| | ethylene: 61 wt. % |
| | ENB: 5 wt. % |

Intrinsic viscosity in ortho-dichlorobenzene at 140° C.: $[\eta]=1.78$ dl/g

| | | |
|---|---|---|
| DSC (2nd heating): | glass transition temperature: | $T_g = -48°$ C. |
| | enthalpy of fusion: | $H_m = 42$ J/g |
| | melting peak: | $T_{m1} = +6°$ C. |
| | | $T_{m2} = +75°$ C. |

Example 49

Ethylene/Propylene/Ethylidenenorbornene Terpolymerization 100 ml of dry n-hexane distilled under inert gas, 10 g of propylene and 2 g of 5-ethylidene-2-norbornene were placed in a dry, oxygen-free 300 ml V4A steel autoclave. At an internal temperature of 50° C., the pressure was raised from 4 bar to 6.5 bar with ethylene. The catalyst used was $2.5 \times 10^{-7}$ mol of $[(flu)Et_2PB(C_6F_5)_2(cp)ZrCl_2]$ (compound no. 31) in 1.65 ml of a 10% toluene solution of MAO (2.5 mmol). The catalyst was added by means of a pressure lock and the pressure was raised from 6.5 bar to 9 bar. The polymerization took place over the temperature range 50°–55° C. and was stopped after 30 minutes. The polymer formed was extracted by stirring with 90/10 ethanol/hydrochloric acid, filtered off, washed with ethanol and dried to constant weight in a vacuum drying cabinet at 80° C.

Polymer yield: 7.5 g

| | |
|---|---|
| Catalyst activity: | 60.0 tons of EP rubber per mol of Zr per hour |
| FTIR: | propylene: 39 wt. % |
| | ethylene: 53 wt. % |
| | ENB: 8 wt. % |

Intrinsic viscosity in ortho-dichlorobenzene at 140° C.: $[\eta]=2.32$ dl/g

| | | |
|---|---|---|
| GC (universal calibration using polystyrene standards): | | $M_w = 239$ kg/mol |
| | | $M_n = 107$ kg/mol |
| DSC (2nd heating): | glass transition temperature: | $T_g = -47°$ C. |
| | enthalpy of fusion: | $H_m = 10$ J/g |
| | melting peak: | $T_m = 10°$ C. |

Comparative Example 1 (Propylene Polymerization)

Approx. 1 mol of propylene was placed in a dry, oxygen-free 300 ml V4A steel autoclave and bulk polymerization was started at 20° C. by adding the catalyst by means of a pressure lock. The catalyst used was $1 \times 10^{-6}$ mol of $[(Me_3Si-cp)Ph_2PBCl_2(Cp)ZrCl_2]$ and $1 \times 10^{-2}$ mol of MAO in 9 ml of toluene.

The internal temperature rose from 20° to 24° C. After one hour, the product was worked up with ethanol/hydrochloric acid and dried and 3.2 g of a rubbery polypropylene were isolated.

| | |
|---|---|
| Catalyst activity: | 3.2 tons per mol · h |
| DSC: | amorphous PP, $T_g = -4°$ C. |
| GC (polystyrene calibration): | $M_w = 143$ kg/mol |
| | $M_n = 28$ kg/mol |
| Intrinsic viscosity (o-Cl$_2$-benzene, 140° C.): | $\eta = 0.66$ dl/g |
| NMR (triad analysis): | 37% isotactic |
| | 42% atactic |
| | 21% syndiotactic |

The markedly lower molecular weight and catalyst activity are evident here.

Comparative Example 2 (Ethylene/propylene Copolymerization)

100 ml of dry toluene distilled under inert gas and 10 g of propylene were placed in a dry, oxygen-free 300 ml V4A steel autoclave. The catalyst was added at 20° C. under pressure by means of a pressure lock and the internal pressure was immediately raised from 2.5 bar to 6.5 bar with ethylene. The internal temperature rose to 28° C. The catalyst used was a mixture of $5 \times 10^{-7}$ mol of $[(Me_3Si-cp)Ph_2PBCl_2(cp)ZrCl_2]$ and $5 \times 10^{-3}$ mol of methylaluminoxane (MAO) in 4.1 ml of toluene, preformed for approx. 10 minutes at room temperature.

The polymerization was stopped after 30 minutes.

| | |
|---|---|
| Polymer yield: | 5.2 g |
| Catalyst activity: | 20.8 tons of EP rubber per mol of catalyst per hour |

Intrinsic viscosity in ortho-dichlorobenzene at 140° C.: $[\eta]=1.51$ dl/g

| | |
|---|---|
| GC in ortho-dichlorobenzene at 140° C.: | $M_w = 309$ kg/mol, $M_n = 106$ kg/mol |
| IR: | 46 wt. % of propylene, 54 wt. % of ethylene |
| DSC: | amorphous copolymer of $T_g = -55°$ C. |

In view of the low polymerization temperature, the observed molecular weight is unsatisfactory and will become markedly worse at higher polymerization temperatures.

Comparative Example 3 (Ethylene/Propylene/Ethylidenenorbornene Terpolymerization)

The procedure of Comparative Example 2 was followed except that the catalyst used was $5 \times 10^{-7}$ mol of rac-[(ind)Et$_2$PBCl$_2$(ind)ZrCl$_2$] activated with $5 \times 10^{-3}$ mol of MAO. The internal pressure was raised by 2 bar with ethylene. The polymerization took place in the presence of 1 g of ethylidenenorbornene (ENB). The terpolymer formed (1.5 g) contained 63 wt. % of ethylene, 35 wt. % of propylene and 2 wt. % of ENB. The intrinsic viscosity in ortho-dichlorobenzene at 140° C. was 1.86 dl/g. The GC measurement in o-Cl$_2$-benzene at 140° C. gave M$_w$=460 kg/mol and M$_n$=203 kg/mol. The DSC measurement in the 2nd heating indicated an amorphous polymer with a glass transition temperature T$_g$ of −50° C.

In view of the low polymerization temperature, the observed molecular weight is unsatisfactory and will become markedly worse at higher polymerization temperatures.

Comparative Example 4 (Ethylene/Propylene/ENB Terpolymerization)

The procedure of the previous Example was followed except that the amount of MAO was only 1×10$^{-3}$ mol and the polymerization temperature was 40 to 45° C. The catalyst activity was 4.4 tons of EPDM per mol of catalyst per hour. The intrinsic viscosity (o-Cl$_2$-benzene, 140° C.) was 1.34 dl/g. The glass transition temperature T$_g$ was −52° C.

The low activity and molecular weight are evident.

Comparative Example 5 (Ethylene/Propylene/ENB Terpolymerization)

The procedure of the previous Example was followed except that the polymerization was carried out at 40 to 46° C. in the presence of 2 g of ENB and with 5×10$^{-3}$ mol of MAO. The catalyst activity was 11.2 tons of EPDM rubber per mol of catalyst per hour. The η value (o-Cl$_2$-benzene, 140° C.) was 1.50 dl/g. M$_w$=302 kg/mol, M$_n$=112 kg/mol.

The copolymer composition was: 69 wt. % of ethylene, 28 wt. % of propylene, 3 wt. % of ENB. The glass transition temperature T$_g$ was −42° C.

Low activity coupled with unsatisfactory incorporation of ENB.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A transition metal compound comprising at least two π systems and at least one donor-acceptor interaction between said at least two π systems, wherein said transition metal compound comprises at least one fluorine-substituted aryl group on at least one acceptor atom.

2. A transition metal compound according to claim 1, wherein the acceptor group contains as the acceptor atom an element of group XIII of the periodic table of the elements as defined by IUPAC, 1985.

3. A transition metal compound according to claim 1, wherein all the substituents on the acceptor atom are fluorine-substituted aryl groups.

4. A transition metal compound according to claim 3, wherein the fluorine-substituted aryl group is perfluorinated.

5. A transition metal compound according to claim 4, wherein the fluorine-substituted aryl group is a perfluorophenyl substituent.

6. A transition metal compound according to claim 1, wherein the π systems are cyclopentadienyl, indenyl, fluorenyl ligands or mixtures thereof.

7. Catalysts comprising transition metal compounds with at least two π systems and at least one donor-acceptor interaction between said at least two π systems, wherein said transition metal compounds have at least one fluorine-substituted aryl group on at least one acceptor atom.

8. Reaction products of co-catalysts comprising transition metal compounds which comprise at least two π systems and at least one donor-acceptor interaction between said at least two π systems, wherein said transition metal compounds have at least one fluorine-substituted aryl group on at least one acceptor atom.

9. A process for the homopolymerization or copolymerization of one or more olefins, i-olefins, alkynes or diolefins as monomers, or for ring-opening polyaddition, in the gas, solution, bulk, high-pressure or slurry phase, at −60 to +250° C., comprising the step of carrying out polymerization in the presence of at least one transition metal compound comprising at least two π systems and at least one donor-acceptor interaction between said at least two π systems, wherein said transition metal compound comprises at least one fluorine-substituted aryl group on at least one acceptor atom.

10. A process according to claim 9, characterized in that it is carried out in the presence of one or more co-catalysts.

11. A process for the homopolymerization or copolymerization of one or more olefins, 1-olefins, alkynes or diolefins as monomers, or for ring-opening polyaddition, in the gas, solution, bulk, high-pressure or slurry phase, at −60 to +250° C., comprising the step of carrying out polymerization in the presence of a reaction product of cocatalysts with transition metal compounds comprising at least two π systems and at least one donor-acceptor interaction between said at least two π systems, wherein said transition metal compound comprises at least one fluorine-substituted aryl group on at least one acceptor atom.

12. A process according to one of claim 11, wherein the transition metal compounds and/or the co-catalysts are applied to a support before polymerization and then used in supported form.

13. A process for the preparation of ultrahigh-molecular weight polyethylene having a M$_w$≧10$^6$ g/mol comprising the step of carrying out polymerization in the presence of at least one transition metal compound comprising at least two π systems and at least one donor-acceptor interaction between said at least two π systems, wherein said transition metal compound comprises at least one fluorine-substituted aryl group on at least one acceptor atom.

14. A process for the preparation of EPDM comprising the step of carrying out polymerization in the presence of at least one transition metal compound comprising at least two π systems and at least one donor-acceptor interaction between said at least two π systems, wherein said transition metal compound comprises at least one fluorine-substituted aryl group on at least one acceptor atom.

15. A process according to claim 14, wherein said EPDM is a high-molecular EP(D)M of M$_w$≧10$^5$ g/mol.

16. A process according to claim 14, wherein said EPDM is an ultrahigh-molecular EP(D)M of M$_w$≧10$^6$ g/mol.

17. A process for the preparation of polypropylene comprising the step of carrying out polymerization in the presence of at least one transition metal compound comprising at least two π systems and at least one donor-acceptor interaction between said at least two π systems, wherein said transition metal compound comprises at least one fluorine-substituted aryl group on at least one acceptor atom.

18. A process according to claim 17, wherein said polypropylene is a high-molecular polypropylene of M$_w$≧10$^5$ g/mol.

19. A process according to claim 17, wherein said polypropylene is an ultrahigh-molecular polypropylene of M$_w$≧10$^6$ g/mol.

20. A process according to claim 17, wherein said polypropylene is an atactic high-molecular polypropylene of M$_w$≧10$^5$ g/mol.

21. A process for the preparation of long-chain branched polymers comprising the step of carrying out polymerization in the presence of at least one transition metal compound comprising at least two π systems and at least one donor-acceptor interaction between said at least two π systems, wherein said transition metal compound comprises at least one fluorine-substituted aryl group on at least one acceptor atom.

* * * * *